(12) United States Patent
Chubykin et al.

(10) Patent No.: US 10,324,080 B2
(45) Date of Patent: Jun. 18, 2019

(54) SYSTEMS AND METHODS FOR AUTOMATED IMAGE-GUIDED PATCH-CLAMP ELECTROPHYSIOLOGY IN VITRO

(71) Applicant: Purdue Research Foundation, West Lafayette, IN (US)

(72) Inventors: Alexander A. Chubykin, West Lafayette, IN (US); Zhaolun Su, Ann Arbor, MI (US); Qiuyu Wu, Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 157 days.

(21) Appl. No.: 15/353,719

(22) Filed: Nov. 16, 2016

(65) Prior Publication Data

US 2017/0138926 A1     May 18, 2017

Related U.S. Application Data

(60) Provisional application No. 62/256,657, filed on Nov. 17, 2015.

(51) Int. Cl.
*G01N 33/48*     (2006.01)
*G01N 33/487*     (2006.01)

(52) U.S. Cl.
CPC .............................. *G01N 33/48728* (2013.01)

(58) Field of Classification Search
CPC ........... G01N 33/5058; G01N 33/5088; G01N 2500/04; G01N 2500/10; G01N 2800/042; G01N 2800/28; G01N 2800/52; G01N 33/5008; G01N 33/5041; G01N 33/5061; G01N 33/6872; G01N 2800/50; G01N 33/5005; G01N 33/5014; G01N 33/5073; G01N 33/5082; G01N 33/6854;
(Continued)

(56) References Cited

U.S. PATENT DOCUMENTS 4,907,158 A * 3/1990 Kettler .................... C12M 35/00
                                                              382/128
4,932,044 A * 6/1990 Williams ............ G01N 15/1468
                                                              359/392
(Continued)

*Primary Examiner* — Manav Seth
(74) *Attorney, Agent, or Firm* — Reichel Stohry LLP; Natalie J. Dean; Mark C. Reichel

(57) ABSTRACT

Automated, image-guided systems for automatically performing in vitro cell patch clamping are provided. The systems are configured for use with a patch-clamp arrangement and include a camera system for providing images from tissues under investigation and a computer to execute calibration, detection, and whole-cell patching algorithms based on the collected image data. Automated methods for carrying out in vitro cell patch clamping using this automated, image-guided system are also provided and include using images to automatically calibrate a manipulator relative to a tissue of interest, detect and extract coordinates for a plurality of cells, and utilizing the coordinates with a patch-clamp arrangement to automatically move a manipulator directly above each of the plurality of cells and initiate the performance of an automated patch clamp mechanism for each of the plurality of cells driven by the system.

20 Claims, 19 Drawing Sheets

(58) Field of Classification Search
CPC ....... G01N 2021/1721; G01N 21/1717; G01N 2333/43552; G01N 2333/775; G01N 2333/912; G01N 2440/38; G01N 2800/2814; G01N 2800/2842; G01N 2800/30; G01N 2800/302; G01N 2800/324; G01N 2800/325; G01N 2800/326; G01N 30/02; G01N 33/48721; G01N 33/50; G01N 33/502; G01N 33/5023; G01N 33/5044; G01N 33/507; G01N 33/5091; G01N 33/542; G01N 33/54366; G01N 33/5438; G01N 33/564; G01N 33/573; G01N 33/58; G01N 33/582; G01N 33/588; G01N 33/6803; G01N 33/92; G01N 33/48728

See application file for complete search history.

(56) References Cited

U.S. PATENT DOCUMENTS

| | | | | |
|---|---|---|---|---|
| 5,108,926 | A * | 4/1992 | Klebe | A61F 2/105 422/930 |
| 5,874,266 | A * | 2/1999 | Palsson | C12N 5/0087 424/577 |
| 5,989,835 | A * | 11/1999 | Dunlay | G02B 21/365 435/288.3 |
| 6,063,260 | A * | 5/2000 | Olesen | G01N 33/48728 204/415 |
| 6,268,168 | B1 * | 7/2001 | Farb | C12M 29/10 435/283.1 |
| 6,316,153 | B1 * | 11/2001 | Goodman | A61K 9/0097 430/8 |
| 6,470,226 | B1 * | 10/2002 | Olesen | G01N 33/48728 435/287.1 |
| 6,514,722 | B2 * | 2/2003 | Palsson | C12M 35/02 435/29 |
| 6,662,039 | B2 * | 12/2003 | Yuste | A61B 5/0059 250/461.2 |
| 6,713,772 | B2 * | 3/2004 | Goodman | A61K 9/0097 250/492.1 |
| 6,743,576 | B1 * | 6/2004 | Sabry | G06K 9/00127 422/50 |
| 6,762,036 | B2 * | 7/2004 | Farb | G01N 33/48728 435/286.5 |
| 6,956,961 | B2 * | 10/2005 | Cong | G01N 15/14 382/133 |
| 7,268,939 | B1 | 9/2007 | McDowell | |
| 7,300,795 | B2 * | 11/2007 | Koller | C12M 35/02 435/173.5 |
| 7,505,618 | B2 * | 3/2009 | Palsson | C12M 35/02 128/922 |
| 7,546,210 | B2 * | 6/2009 | Callahan | G01N 15/1475 382/133 |
| 7,919,319 | B2 * | 4/2011 | Jervis | C12M 29/04 435/292.1 |
| 8,114,662 | B2 * | 2/2012 | Clark | B82Y 5/00 435/288.7 |
| 8,263,358 | B2 * | 9/2012 | Clark | B82Y 5/00 424/9.6 |
| 8,945,862 | B2 * | 2/2015 | Wu | C12N 5/0603 435/6.1 |
| 8,947,518 | B2 * | 2/2015 | Kiyota | C12M 41/36 348/79 |
| 9,111,343 | B2 * | 8/2015 | Zahniser | G06K 9/00134 |
| 9,150,598 | B2 * | 10/2015 | Schmidt | C07F 9/22 |
| 9,192,630 | B2 * | 11/2015 | Baraban | A61K 35/30 |
| 9,207,237 | B2 * | 12/2015 | Cohen | G01N 33/54373 |
| 9,280,699 | B2 * | 3/2016 | Zahniser | G06K 9/00134 |
| 9,301,952 | B2 * | 4/2016 | Iadonato | C07D 213/85 |
| 9,624,471 | B2 * | 4/2017 | Ruohola-Baker | C12N 15/111 |
| 10,068,126 | B2 * | 9/2018 | Zahniser | G06K 9/00134 |
| 10,163,203 | B2 * | 12/2018 | Nakagawa | C12M 41/46 |
| 2003/0096322 | A1 * | 5/2003 | Giuliano | C12Q 1/68 435/7.21 |
| 2009/0081170 | A1 * | 3/2009 | Riley | A01K 67/0276 424/93.7 |
| 2009/0176260 | A1 * | 7/2009 | Wu | C12N 5/0603 435/8 |
| 2012/0015841 | A1 * | 1/2012 | Shekdar | G01N 33/502 506/9 |
| 2013/0027539 | A1 * | 1/2013 | Kiyota | C12M 41/36 348/79 |
| 2013/0035397 | A1 * | 2/2013 | Iadonato | A61K 31/095 514/685 |
| 2013/0224821 | A1 * | 8/2013 | Deisseroth | G01N 33/5058 435/173.4 |
| 2013/0225963 | A1 * | 8/2013 | Kodandaramaiah | A61B 5/6885 600/373 |
| 2014/0228857 | A1 | 8/2014 | Kodandaramaiah et al. | |

* cited by examiner

| | | |
|---|---|---|
| $R_p$ threshold #1-Initial pipette resistance | <10 MΩ | Pipette tip diameter, clogging |
| P(+) threshold #1- Minimum positive pressure | >30 mmHg | Extracellular matrix composition, target cell depth (higher pressure may be necessary for deeper cells) |
| $R_m$ threshold #2-Touch cell resistance coefficient | >115% of initial $R_p$ | Cell size/type |
| P(-) threshold #1 - negative pressure for sealing | <-60 mmHg | Cell size/type |
| $R_m$ threshold #3-for -70mV adjustment | 100MΩ | Based on experience. May be optimized by data mining. |
| $R_m$ threshold #4-Wait for gigasealing resistance | 200MΩ | Based on experience. May be optimized by data mining. |
| $R_m$ threshold #5-Gigaseal resistance | 1000MΩ | Patch quality requirement. A Higher value will result in the tighter seal. |
| P(-) threshold #2- Minimum negative pressure for break-in | <-85 mmHg | Cell size/type, +/- zapping |
| $R_m$ threshold #6-Broken-in resistance | <300 MΩ | Cell size/type. |
| $I_{hold}$ threshold #1-Broken-in holding current | >-200pA and <100pA | Seal quality |
| t threshold #1-Time to fail | 4 min | Based on experience. |

FIG. 8b

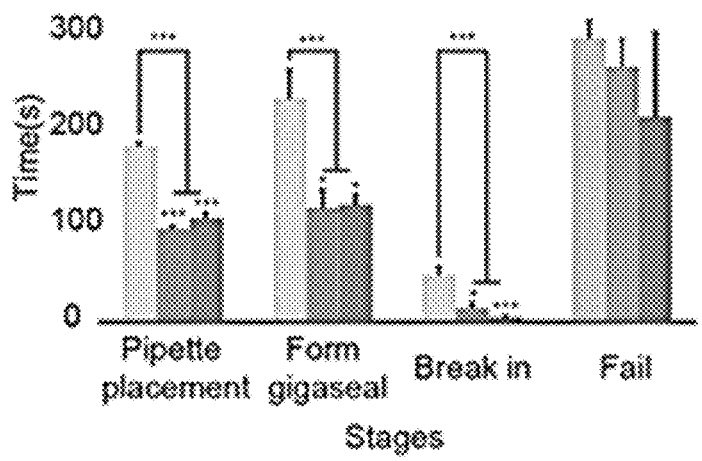

SYSTEMS AND METHODS FOR AUTOMATED IMAGE-GUIDED PATCH-CLAMP ELECTROPHYSIOLOGY IN VITRO

PRIORITY

The present application is related to, and claims the priority benefit of, U.S. Provisional Patent Application Ser. No. 62/256,657, filed Nov. 17, 2015, the contents of which are hereby incorporated into the present disclosure by reference in their entirety.

TECHNICAL FIELD

The present application relates to patch-clamp arrangements and in particular to an automatic vision-guided patch clamp system that can be used in vitro.

BACKGROUND

This section introduces aspects that may help facilitate a better understanding of the disclosure. Accordingly, these statements are to be read in this light and are not to be understood as admissions about what is or is not prior art.

Patch-clamp recording is a gold-standard technique for accurate measurement of membrane voltage fluctuations, synaptic currents and ionic channel activity in neurons. It has allowed neuroscientists to study properties of individual ion channels and synapses and to characterize synaptic plasticity and dendritic integration. Patch-clamp recording has also been essential for dissecting the pathophysiology of neurological disorders caused by mutations in channels and synaptic proteins. In combination with morphological characterization, this method has been used for classifying cell types in the brain and elucidating connectivity among nearby neurons. It has also been successfully coupled with optogenetics and applied to map long-range neuronal circuits.

A typical patch-clamp experiment is highly repetitive, making it strenuous and error-prone for the investigator. Typically, a neuron is first manually located, a micropipette is brought into vicinity of the neuron, and then through incremental one-dimensional movements the micropipette is brought into contact with the neuron by applying a pressure to the neuron's surface. When advancing the micropipette towards the target cell, errors such as advancing the pipette too far into the tissue, breaking the pipette tip, and/or improperly setting the pipette pressure are common among novices and occasional among experienced researchers. Furthermore, these errors usually accumulate toward the end of a day when researchers get tired.

Some steps of the patch-clamp process are difficult to control manually. For example, the delicate pneumatic pressure changes applied to the pipette are necessary to form a whole-cell configuration. This pressure control is typically done by mouth or with syringe, making them difficult to replicate among labs and even among different investigators in the same lab. There is also a plethora of undocumented heuristics, such as the magnitude of pressure, number of pressure pulses, and time to match cell membrane potential (−70 mV), that are challenging to master and vary from lab to lab. This is especially an issue when large datasets collected by various laboratories for a single study must be directly comparable. Further, while the integration of patch-clamp recording with other techniques such as optogenetics is essential for investigating complex circuits in the brain, the additive complexity of the procedure could prohibit new investigators from initiating such projects, despite the high scientific interest and large data set demand.

Prior to the disclosure within the present application, there was no comprehensive solution which automates the patch-clamp procedure in vitro. While fully automated planar patch-clamp systems have been commercially available for years and have been instrumental in high-throughput drug discovery applications, they are only suitable for cells in suspension, but not for neuronal cultures or brain slices. In vivo "blind" patching reported previously was designed to use only electrical resistance, not visual information, as an indicator of cell proximity. However, the electrical resistance measurements are limited to several micrometers of range to successfully detect a neuron. In most of patch-clamp applications targeting cells based on visual cues such as the shape or fluorescence of a cell is required. Prior to the disclosure within the present application, no automation system existed to assist in the performance of such visually-guided patch-clamp experiments in tissue.

There is, therefore an unmet need for an automated patch-clamp system capable of recognizing target cells and identifying location of these cells in order to perform patch-clamp experiments in larger numbers.

BRIEF SUMMARY

In at least one exemplary embodiment of the present disclosure, an automated vision system configured for use with an apparatus for cell patch clamping is provided. The system may comprise a camera system configured to provide images of in vitro tissue positioned on a stage of an apparatus for cell patch clamping and a computer comprising a processor. The computer is in communication with the camera system and configured to: receive a plurality of images from the tissue positioned on the stager from the camera of the system; detect a plurality of cells in each image; extract coordinates of each of the plurality of cells from each image; and provide the coordinates to a stage controller of the apparatus for cell patch clamping to: automatically move a manipulator coupled with the stage controller to a position directly above each of the plurality of cells, and initiate and control an automated patch-clamp process, performed by the apparatus for cell patch clamping, for each of the plurality of cells.

The automated vision system may further comprise a pressure control system in operative communication with the computer and a pressure sensor coupled with the manipulator of the apparatus for cell patch clamping. In at least one embodiment, the pressure control system comprises a pump in fluid communication with one or more valves. The camera system may be coupled with a microscope of the apparatus for cell patch clamping. Additionally or alternatively, the tissue may comprise a brain slice and the plurality of cells may comprise living neurons.

In certain embodiments of the automated vision system, detecting a plurality of cells in each image may further comprise: transforming the plurality of images into corresponding black and white images that apply a plurality of predetermined multiples of mean pixel intensities; extracting contours of various shapes in the black and white images and establishing forms of the various shapes by identifying edges of the various shapes; and identifying targeted cells based on predetermined size and circularity associated with a centroid of each of the various shapes. This may be performed by executing a computer vision algorithm on the processor of the computer or through other modalities. In at least one exemplary embodiment, providing the coordinates to a stage controller further comprises: clustering centroids into groups based on distance and abundance measurements; and calculating a mean of all centroids in a respective cluster according to a standardized coordinate system. There, clustering centroids into groups further comprises superimposing and clustering centroids along x- and y-dimensions.

Additionally or alternatively to the foregoing features, embodiments of the automated vision system may further comprise a computer usable medium having a computer readable program code embodied therein for causing the computer to operate the camera system and the apparatus for cell patch clamping. In such embodiments, the computer readable program code executable by the processor may comprise: a computer readable program code means for operating the camera system; a computer readable program code means for operating the apparatus for cell patch clamping; a computer readable program code means for acquiring data from the apparatus for cell patch clamping; and a computer readable program code means for analyzing images received from the camera system and data received from the apparatus for cell patch clamping and displaying analysis to a user. Still further, the computer may be additionally configured to calibrate a position of the manipulator relative to a coordinate system of the microscope and the computer readable program code further comprises a computer readable program code means for calibrating the position of the manipulator from the plurality of images received from the camera system. There, calibration of the manipulator may comprise: using the camera system to acquire an image of the tip of the manipulator each time the tip is iteratively moved a predefined distance along a x-, y-, or z-dimension; and processing each image of the tip to identify a data point indicative of a coordinate of the tip of the manipulator. The step of processing may comprise: transforming the image into a corresponding black and white image by applying a plurality of predetermined multiples of mean pixel intensities; extracting contour lines of the tip in the black and white image, and identifying a point where the contour lines intersect, with the point where the contour lines intersect being the coordinate of the tip of the manipulator.

Additional automated vision systems configured for use with an apparatus for cell patch clamping are also provided. In such embodiments, the system comprises a camera system configured to provide images and operate in conjunction with an apparatus for cell patch clamping and a computer configured for operable communication with the camera system, an apparatus for cell patch clamping, and a pressure control system in fluid communication with a pressure sensor coupled with a manipulator of the apparatus for cell patch clamping. The computer comprises a processor and a computer usable medium having computer readable program code embodied therein for causing the computer to operate the camera system, the pressure control system, and the apparatus for cell patch clamping. Furthermore, the computer readable program code is executable by the processor and comprises a computer readable program code means for operating the camera system to capture images; a computer readable program code means for operating the apparatus for cell patch clamping to perform whole-cell patch clamp processes and recordings on a plurality of cells within in vitro tissue positioned on a stage of the apparatus for cell patch clamping; a computer readable program code means for operating the pressure control system to apply positive or negative pressure through, or maintain the pressure of, the manipulator of the apparatus for cell patch clamping; a computer readable program code means for receiving data from the apparatus for cell patch clamping; a computer readable program code means for receiving images captured by the camera system; and a computer readable program code means for analyzing images and data received from the camera system and apparatus for cell patch clamping.

Methods for performing whole-cell patch clamping in vitro are also described. In at least one exemplary embodiment of such a method, the method comprises the steps of: using a camera system to capture images of in vitro tissue positioned on a stage of an apparatus for cell patch clamping; accessing the images with a computer, the computer comprising a processor and in communication with the apparatus for cell patch clamping; detecting a plurality of cells in each image using the computer; extracting coordinates of each of the plurality of cells from each image, each of the coordinates associated with a position of a cell on a microscope stage of the apparatus for cell patch clamping; moving a tip of a manipulator of the apparatus for cell patch clamping to a position directly above a targeted cell within the plurality of cells, the position of the tip based on one or more of the coordinates; and initiating the apparatus for cell patch clamping to perform an automated patch clamp process for the targeted cell, at least one step of the patch clamp process controlled by the computer. In at least one embodiment, the methods hereof may additional comprise the steps of: receiving, on the computer, data from the apparatus for cell patch clamping; and analyzing, using the computer, the received data into one or more patch logs, with each of the images captured by the camera system are captured at a different z-section of the in vitro tissue. Additionally or alternatively, the computer is in operative communication with a pressure control system and a pressure sensor coupled with the manipulator. There, the automated patch clamp process additionally comprises the steps of: and a pressure sensor coupled with the manipulator and the automated patch clamp process comprises the steps of: iteratively lowering the tip of the manipulator; operating the pressure control system to apply positive pressure through the tip of the manipulator; measuring the resistance at the tip after each iteration of the lowering step; determining if a cell has been encountered by the tip by taking into account the coordinates and the resistance measurements after each iteration of the lowering step; iteratively continuing the steps of lowering and determining until the resistance measurement satisfies a first pre-set threshold value; and when the resistance measurement satisfies the first pre-set threshold value, operating the pressure control system to apply negative pressure to the targeted cell through the tip of the manipulator. In such embodiments, the lowering, measuring, and determining steps are automated and controlled by the computer.

In addition to the foregoing steps, the method may additionally comprise the step of initiating the formation of a gigaseal between the tip of the manipulator and the targeted cell by continuing the step of operating the pressure control system to apply negative pressure to the targeted cell until the resistance measurement satisfies a second pre-set threshold value. When the resistance measurement satisfies the second pre-set threshold value, the method further comprises operating the pressure control system to match a holding voltage potential of the manipulator with a resting membrane potential of the targeted cell, and ceasing the application of negative pressure to the targeted cell. The method may also comprise the steps of: prompting a user to select a process for establishing a whole-cell patch clamp configuration from one or more options comprising a long suction approach, a zap approach, and a combination of a long suction and zap approach; and performing the process for establishing a whole-cell patch clamp configuration pursuant to the user-selected option; or, if the user does not select an option within a pre-set period of time, performing the process for establishing a whole-cell patch clamp configuration pursuant to a pre-set default option.

In certain embodiments, the detection step of the methods disclosed herein may optionally comprise: transforming each image into a corresponding black and white image by applying a plurality of predetermined multiples of mean pixel intensities; extracting contours of various shapes in each black and white image and establishing forms of the various shapes by identifying edges of the various shapes; and identifying targeted cells based on predetermined size and circularity associated with a centroid of each of the various shapes. The step of moving a tip of a manipulator may also further comprise the steps of: clustering centroids into groups based on distance and abundance measurements by superimposing and clustering centroids along x- and y-dimensions; and calculating a mean of all centroids in a respective cluster according to a standardized coordinate system.

Additionally, the methods hereof may further comprise the steps of: using the camera system to acquire an image of the tip of the manipulator each time the tip is iteratively moved a predefined distance along a x-, y-, or z-dimension; and processing each image to identify a data point indicative of a coordinate of the tip of the manipulator, the step of processing comprising the steps of: transforming the image into a corresponding black and white image by applying a plurality of predetermined multiples of mean pixel intensities; extracting contour lines of the tip in the black and white image, and identifying a point where the contour lines intersect. There, the point where the contour lines intersect is the coordinate of the tip of the manipulator. Still further, the methods hereof may be designed such that the processing step is performed at least two times for each image.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 8*b* is a table of exemplary default threshold values for use in the patch function algorithm of FIG. 8*a*;

FIGS. 9*a*-9*d* show graphical and other data supporting that the automated patching algorithm of the present disclosure significantly improves patch clamp efficiency, with FIG. 9a showing average time spent during pipette placement, forming gigaseal, and establishing whole-cell configuration (break-in) in both automatic patching (darkest bar) and semi-automatic patching (middle bar) is significantly shorter than manual patching (lightest bar) in successful trials (time from the end of pipette placement to termination of a failed trial was not significantly different between the two methods), FIG. 9b showing a pie chart displaying success rates for automatic and manual patching, FIG. 9c displaying a dot matrix representative of distribution times spent during the three patching steps and supporting that automatic patching steps are faster and more reproducible as compared to the manual patching steps (data points are the times for pipette placement in all successful trials versus gigaseal time (top) and break-in time (bottom), and FIG. 9d showing a schematic illustration depicting the average time and success/failure rates of automatic and manual patching;

FIGS. 10e-10h illustrate data relating to the successful use of method 800 for automated patching and recording of two or more cells simultaneously, with FIG. 10e showing an image of two simultaneously patched cells, FIG. 10f showing a confocal image of the two cells shown in FIG. 10e filled with Alexa 568 hydrazide and fixed after patching, FIG. 10g showing a graph of the electrophysiological responses of these two patched cells to hyperpolarizing and depolarizing current injections, and FIG. 10h showing data for simultaneous recordings of excitatory postsynaptic potentisl (EPSPs) from these two neurons evoked by white matter (WM) stimulation.

Figure 1A:
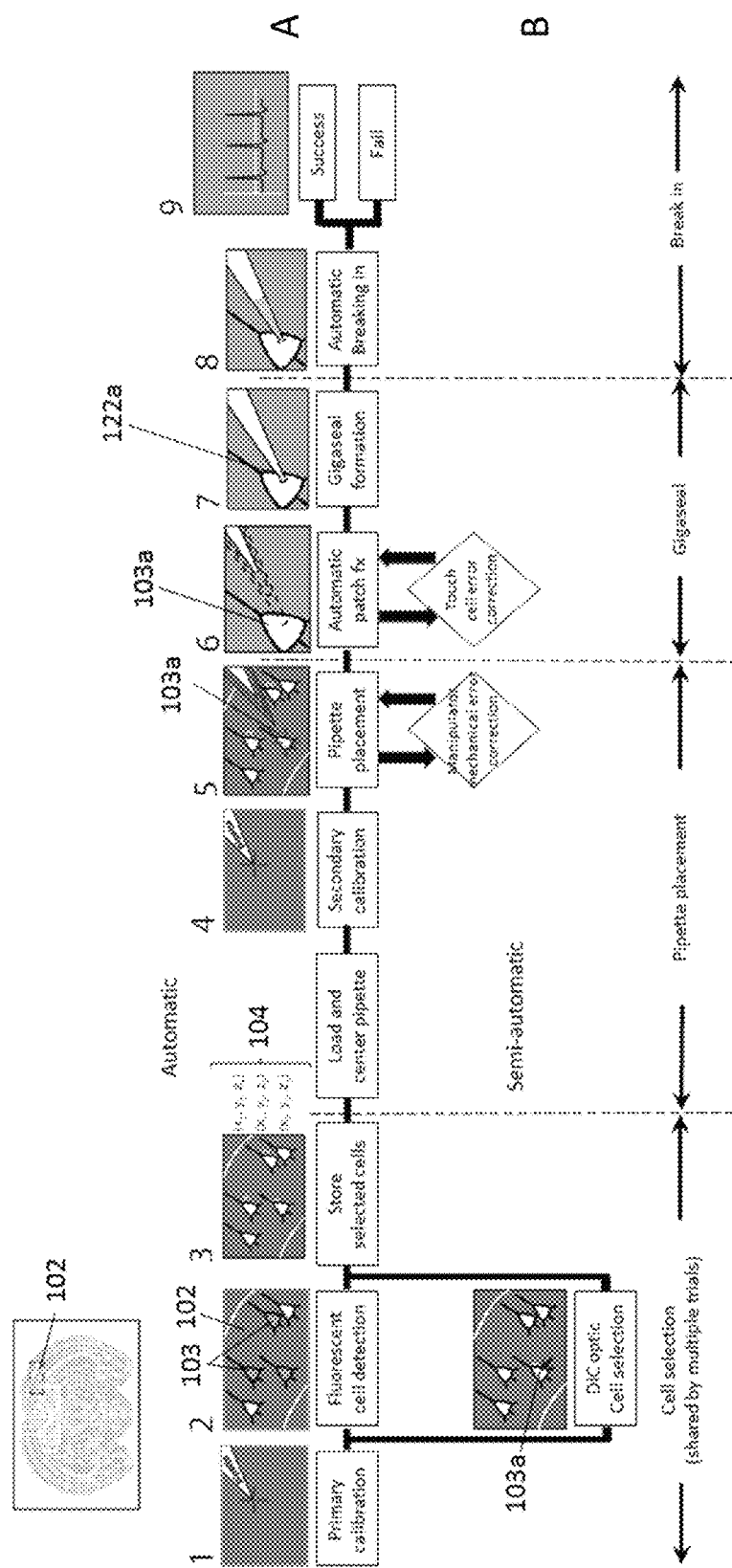
FIG. 1*a* shows steps in an automated patch-claim method according to an exemplary embodiment of the present disclosure, with panels labeled as follows: 1) primary calibration; 2) target cell selection; 3) selected cell coordinates stored for further patching; 4) secondary calibration; 5) pipette placement; 6) patch algorithm initiation; 7) gigaseal formation; 8) break-in; and 9) whole-cell recording.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended by the description of these embodiments. On the contrary, many modifications and other embodiments of the technology described herein will come to mind to one of skill in the art to which the present disclosure pertains having the benefit of the teachings presented in the present descriptions and associated figures. Therefore, it is understood that this disclosure covers any such alternatives, modifications, and equivalents as may be included within the spirit and scope of this application as defined by the specification and appended claims. As previously noted, while this technology may be illustrated and described in one or more preferred embodiments, the devices, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the device and system components of the present disclosure may be tailored in furtherance of the desired application thereof.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

Neurons are heterogeneous cells; namely, individual neurons can express many different sets of genes, comprise different shapes and change in different ways in response to different brain disorders, which presents a significant obstacle to understanding how neurons compute and identifying markers of disease. Along these lines, one of the critical questions in neuroscience at the time of this disclosure is how brain neural networks perform computations necessary for higher level cognitive functions. To answer this, recordation of the electrical activity of individual neurons with synaptic resolution is required. Conventionally, the whole-cell patch clamp technique has been employed to characterize multiple aspects of excitatory and inhibitory synaptic currents, cellular excitability, and interneuronal connectivity. However, this technique is slow, requires a high degree of experience and skill as many of the steps are performed manually, and comprises numerous variables that are difficult to measure and/or replicate in subsequent experiments.

The present disclosure provides novel patch-clamp systems, and methods of using the same, that are capable of automatically recognizing and identifying the location of target cells using image-guided techniques, and subsequently performing automated patch-clamp experiments in large numbers. Notably, the automated and visually guided aspects of these systems and methods reduce the need for manual intervention by automating highly skilled, but repetitive, tasks, thus allowing users to maximize the amount of data that can be obtained during electrophysiological trials, while using less-skilled users to perform the collection of data. Automation and visualization also increases the speed and throughput of electrophysiological trials, while reducing errors associated with manual manipulations and variable analysis. By minimizing manual manipulations, protocols that require complex, fast, or repetitive steps may be preprogrammed and executed consistently and reliably. A brief overview of the systems and methods hereof will first be described, followed by a more in-depth description of system components and modules and the steps associated with using the same to perform automated patch-clamp processes.

Figure 1B:
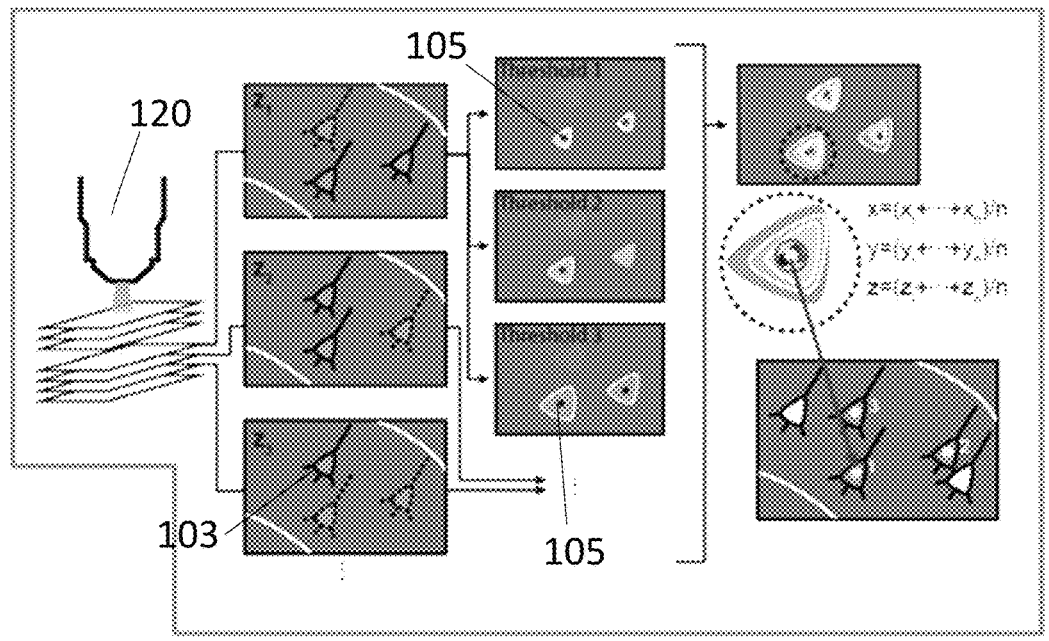
FIGS. 1*b* and 1*c* show schematic depictions of a computer vision algorithm according to an exemplary embodiment of the present disclosure.
Figure 1C:
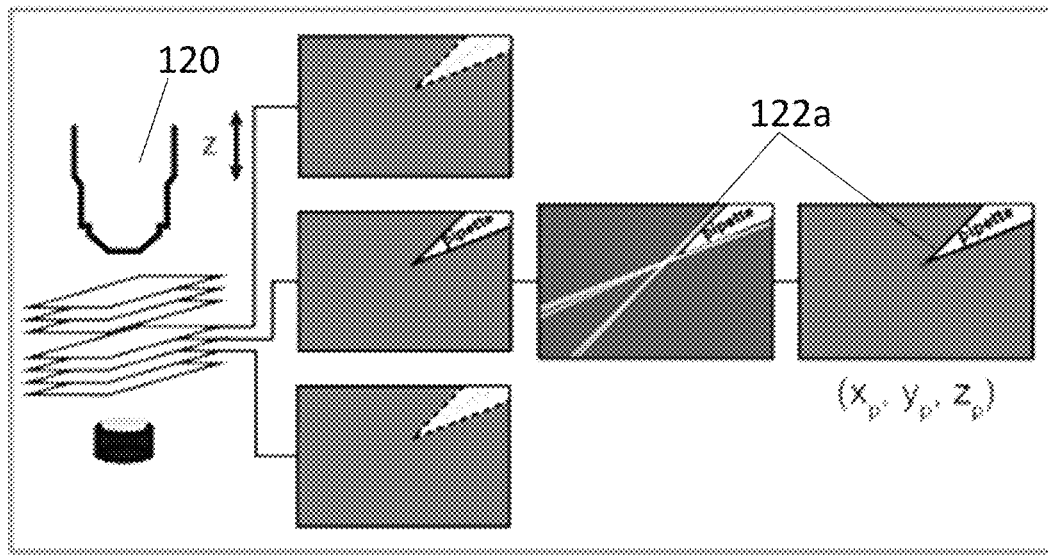

Referring to FIGS. 1a, 1b, and 1c, schematic representations are provided showing an automated imaged guided (IG) patch-clamp system 100 (herein referred to as "Autopatcher IG system 100" or "system 100") that enables an electrophysiology rig (or similar device) to automatically perform patch-clamp recordings in vitro from individual neurons 103 located in a brain slice 102. The inventive technology of the present disclosure uses computer vision and requires no manual participation, which makes the whole-cell patch clamp technique faster, easier to perform, and accessible for less experienced users.

Generally, the Autopatcher IG system 100 comprises both hardware and software components, with the software reducing the need for manual intervention by automatically manipulating components of the hardware to automate steps in the patch-clamp recording process. For example, the system 100 hereof is configured to automate cell detection (FIG. 1b), pipette calibration (FIG. 1c), manipulator trajectory planning and execution, pneumatic pressure control, electrophysiological measurements, and data logging using image-guided methodologies.

Performing an automated patch-clamp process in vitro using the Autopatcher IG system 100 includes a series of automated steps, general embodiments of which are illustrated in the panels identified as 1-9 in FIG. 1a. Primarily, visual, cortical brain slices 102 (comprising living tissue) from a mammal are prepared using methodologies known in the art. A targeted brain slice 102 is prepared (see unlabeled brain panel in FIG. 1a) and primary calibration is done automatically through computer vision (panel 1; see also FIG. 1c). As shown in panel 2, a target cell 103a is selected using either mouse clicks (lower panel in semi-automatic section) or automatic fluorescent cell detection (upper panel; see also FIG. 1b showing additional detail of this step). For example, in at least one embodiment, the centroids 105 of the identified cell contours for each threshold within the brain slice 102 are superimposed and clustered along x- and y-dimensions, and final cell coordinates 104 for the cells 103 within the visual field are computed as the average of the corresponding x-, y-, and z-cluster coordinates. The coordinates 104 of the cells 103 are then stored by the system 100 for use with the patching process, with subscripts indicating the cell ID number (panel 3; see also FIG. 1b).

Additionally, the system 100 is configured to perform secondary calibration of a manipulator 122 relative to the slide and selected cell 103a (i.e. determine the precise coordinates of a tip 122a of a pipette 121 within the view of a microscope) using a computer vision algorithm (panel 4; see also FIG. 1c showing additional detail of this step). This secondary calibration step determines the coordinates 104 of the patch pipette with micrometer scale accuracy and resolution (indicated in panel 4 by the crosshairs).

With the coordinates of the tip 122a and target neuron(s) 103a determined, the system 100 uses a manipulator trajectory planning and movement algorithm to determine the trajectory to be taken by the manipulator(s) and automatically guides the manipulator(s) 122 to a location adjacent to the selected cell(s) 103a (panel 5). The patch algorithm is then initiated, which results in advancement of each manipulator 122 in small increments towards the selected cell 103a (panel 6; see FIG. 8a for a detailed flow chart). During this process, the system 100 monitors the resistance change adjacent to the tip 122a of the pipette 122 by emitting a series of test current injections. Using impedance measurements (i.e. when the appropriate resistance change is detected), close contact is achieved between the membrane or boundary of the selected cell 103a and the tip 122a of the manipulator 122 to form a gigaseal (panel 7). The steps illustrated in panel 7 of FIG. 1a may be performed through further advancement of the manipulator 122 under computer-guided control, the application of suction through the manipulator 122, or both. Furthermore, a series of images along the optical z-axis may be acquired during performance of the steps depicted in panel 6 to determine if the pipette tip 122a is in focus and ensure accuracy. Additionally or alternatively, the computer vision processing steps (depicted in both panels 4 and 6) may also include local contrast detection, Gaussian blur, Canny edge detection, and Hough transform, for example.

After a gigaseal is established, the membrane of a selected cell 103a is ruptured (using the current injection through the patch electrode and/or a pulse of suction delivered through the tip thereof) such that the tip of the manipulator 122 breaks into the cell 103a (panel 8) and whole-cell recording is performed on the cell 103a (panel 9) and/or additional cellular data can be collected therefrom.

As described herein, a fully automatic patching process is the successful automatic execution of all steps from loading a new manipulator/pipette to obtaining a whole cell patch (starting at panel 1 and ending at panel 9, success; labeled row A in FIG. 1a). If adjustments are to be made at any point to this automatic process, it is defined as a semi-automatic patching trial and includes one or more steps in row B of FIG. 1a. Such adjustments are typically manipulator 122 mechanical error correction, caused by incorrect cell contact detection.

As is described in additional detail below, performance of system 100 has been validated, at least in part, through performing patch-clamp recordings of over 200 cells in mouse brain slices from wild-type, transgenic, and viral injected mice. Such validation experiments support the robust and broad application of the system 100 in various slice physiology experimental designs.

Figure 2A:
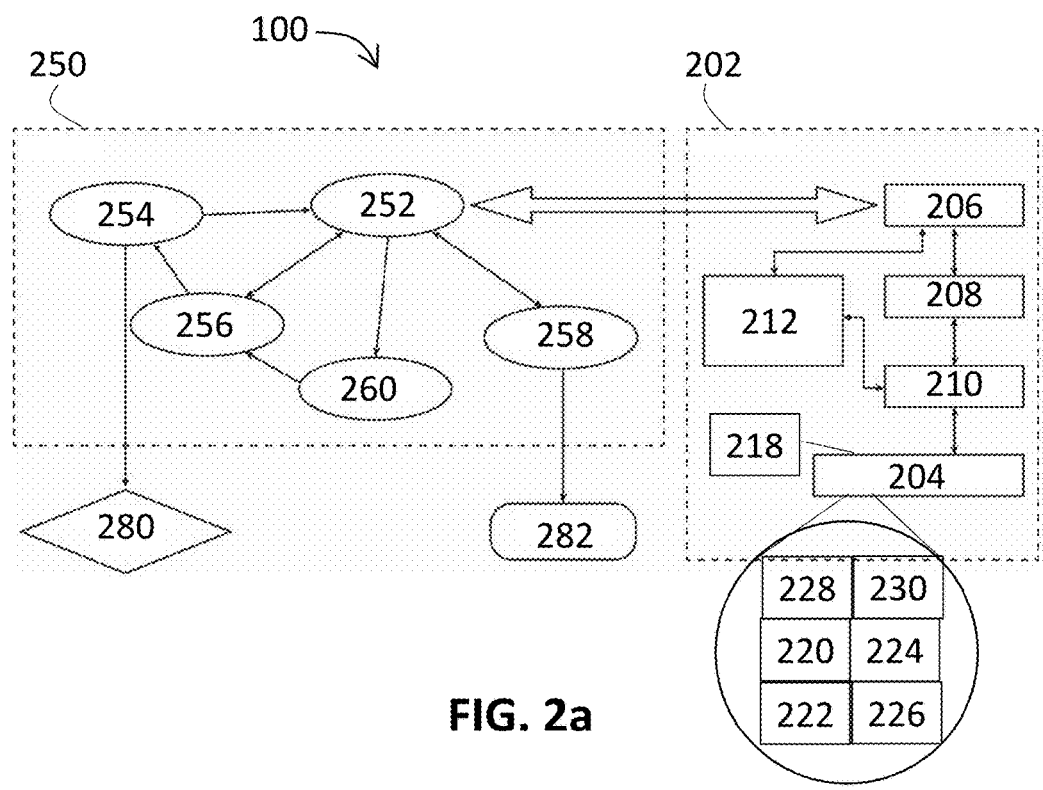
FIG. 2*a* shows a block diagram of a whole-cell patch clamp system according to an exemplary embodiment of the present disclosure.
Figure 2B:
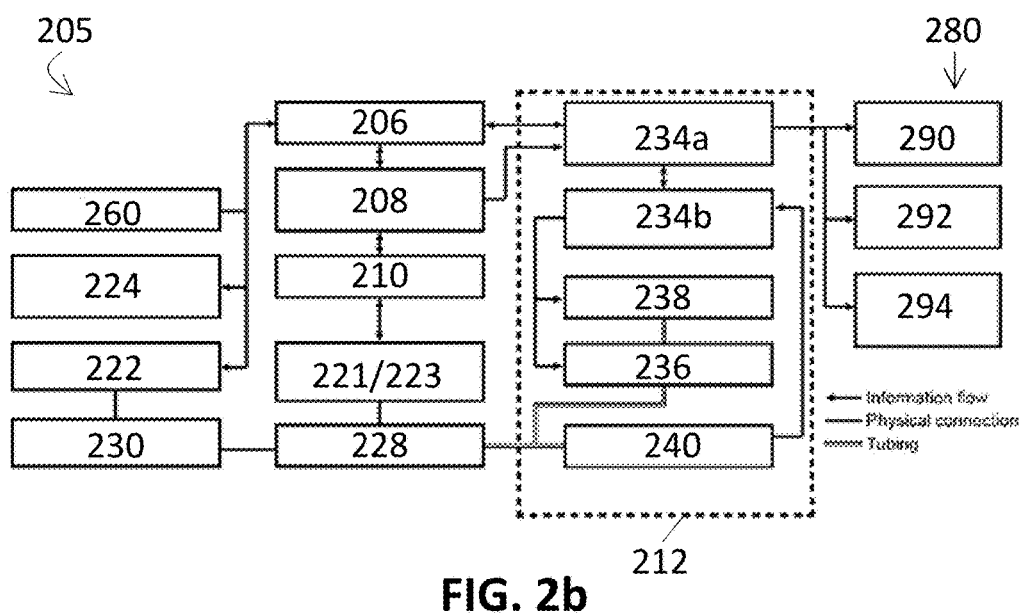
FIG. 2*b* shows a block diagram of a hardware set up for the patch clamp system of FIG. 2*a* according to an exemplary embodiment of the present disclosure.
Figure 2C:
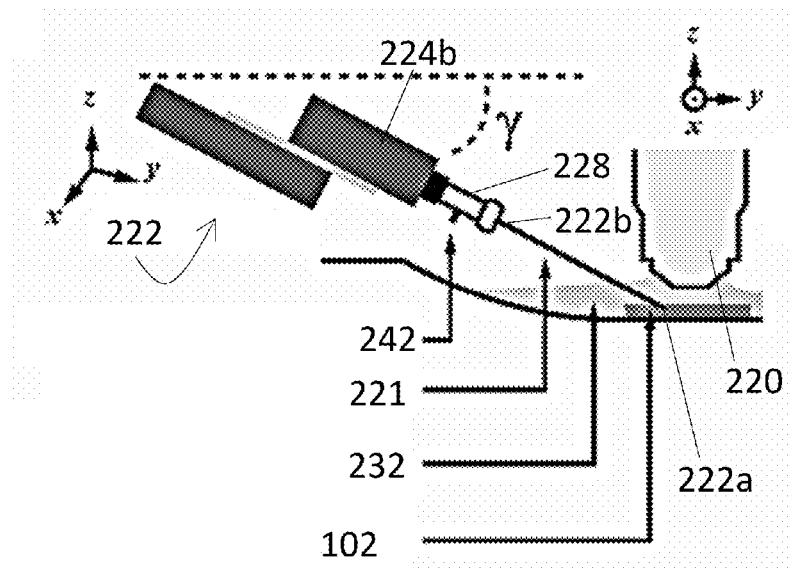
FIG. 2*c* shows how standard patch-clamp electrophysiology equipment is used in conjunction with a pressure control system and custom software protocols according to an exemplary embodiment of the present disclosure.

Now referring to FIGS. 2a-2c, the Autopatcher IG system 100 comprises both hardware 202 and software 250. FIG. 2a shows a high-level block diagram depicting the interface between the hardware 202 and software 250 of the system 100. In at least one embodiment, the hardware 202 block of the system 100 comprises an electrophysiology rig 204 in communication with a computer 206, a data acquisition system 208, an amplifier 210, and a pressure control system 212. These components are coupled and/or in communication with each other and, in turn communicate or are controlled through, the computer 206 via the software 250. Likewise, the software 250 block of the Autopatcher IG system 100 comprises the main graphical user interface ("GUI") 252, the command sequence module 254, memory 256, patch control module 258, and camera module 260, and provides communication with (and allows for operation of) peripheral devices 280 and controls patch-clamp data logging 282. It will be appreciated that while standard patch-clamp electrophysiology equipment may be used in conjunction with the hardware 202 of the system 100, and the software 250 is custom-made according to the present disclosure. The system 100 may not necessarily comprise all of the aforementioned software 250 modules, but instead only the minimum necessary to control the hardware 202 and execute the necessary automated image-guided patch-clamp process steps described herein.

In general, the system 100 is widely adaptable as the software 250 is suitable for a broad range of hardware 205 configurations augmented only by a pressure control system 212. The abstracted structure of the code allows for simple driver programming such that, in addition to the hardware 202 options particularly described herein, the Autopatcher IG system 100 can also be implemented to hardware systems different from that which is described (i.e. unsupported devices). Indeed, the Autopatcher IG system 100 is organized in a modular style with the capability of easy functional expansion. Different modules communicate with each other through the main module and can run independently. The software 250 is designed to support device driver abstraction—i.e., if a user needs to implement a different camera 218, manipulator 222, pressure control system 212, and/or other hardware 202 component than what is described herein or currently being used, the software 250 of the system 100 is designed such that few changes to the code thereof are required beyond the replacement of low-level device commands.

Referring back to FIG. 2a, the electrophysiology rig 204 of the system 100 may comprise any patch-clamp in vitro electrophysiology rig (comprising a conventional off-the-shelf setup or otherwise). In at least one embodiment, the electrophysiology rig 204 comprises an upright microscope 220 outfitted with differential interference contrast (DIC) optics or the like, one or more manipulators 222 (e.g., a patch pipette 221 and/or a pipette micromanipulator), holder(s) 228, one or more stages 224 (e.g. a microscope stage 224a, a headstage 224b, etc.), one or more mounting platforms 226, and a motorized 3-axis control 230. Image guidance is accomplished by interfacing a camera 218 with the microscope 220 (e.g., a charge-coupled device (CCD) camera).

Likewise, the microscope 220 may comprise any microscope suitable for in vitro patch clamp applications and, in at least one embodiment comprises low-magnification (4×/10×) and high-magnification (40×/60×) water-immersion objectives (e.g., OLYMPUS or NIKON) that can be exchanged manually using a swinging nosepiece or automatically using a motorized carriage. The 3-axis control 230 comprises a 3-axis actuator and motor (linear or otherwise), is computer-controlled, and functions to move and control at least one of the stage(s) 224 and/or manipulator(s) 222 coupled therewith (e.g., a microscope stage 224a, a headstage 224b coupled with a manipulator 222, and/or a pipette micromanipulator 222). For example, in at least one exemplary embodiment, the 3-axis control 230 functions to move a pipette tip 222a up and down in a precise manner for positioning the same.

The manipulators 222 comprise the various tools of the rig 204 that may be operated to manipulate, express from, or deliver compounds to the tissue under examination on the stage. It will be appreciated that a single manipulator 222 may be utilized by the system 100 for a single or any number of applications. For example, in at least one embodiment, a single manipulator 222 may be used only to perform the patch clamp process or to deliver a chemical compound to a targeted cell 103a. Alternatively, the same manipulator 222 may be used to patch a cell 103, infuse DNA, peptides, other chemical compounds, and/or drugs into the internal part of the patched cell 103, and/or to remove cellular material from the patched cell 103.

At least one of the manipulators 222 comprises a pipette 221, which is a glass microneedle comprising a proximal end 222b, a distal end having a hollow tip 222a, and defining a lumen therethrough. The pipette 221 (and/or headstage 224b coupled thereto) comprises at least one recording electrode 223 (which may be positioned within the pipette holder 228 in at least one embodiment, and connected to a patch clamp amplifier 210 as is known in the art). In at least one embodiment, the electrode 223 comprises a silver-chloride electrode and, additionally or alternatively, is configured to measure one or more parameters such as resistance and/or voltage, for example. (At least one other ground electrode may be positioned within a bath 232 formed by mounting platform 226 and/or an open bath chamber and containing a fluid such as oxygenated artificial cerebralspinal fluid, for example.) The hollow tip 222a may, in at least one embodiment, be about 1 micron wide and the pipette 221 may comprise a micropipette. A vacuum source (not shown) may be coupled with the pipette 221 such that suction can be applied therethrough and communicated through the tip 222a.

Further, a holder 228 is used to couple the manipulator 222 (e.g., via the proximal end 222b of the pipette 221) with an amplifier 210 via a headstage 224b as shown in FIGS. 2b and 2c. The amplifier 210 is computer-controlled, receives input from the headstage 224b, and may be a single- or multi-channel amplifier suitable for electrophysiology purposes that allows for recordings from one cell or simultaneous recordings from multiple cells, respectively. In at least one embodiment, the amplifier 210 may comprise any computer-controlled patch-clamp amplifier (e.g., such as MULTICLAMP 700B or AXOPATCH 200B) and may comprise independent headstages, feedback resistors, automated capacitance and series-resistance compensation, and/or an on-board microprocessor configured to communicate with a host computer (e.g., computer 206) via a cable or otherwise as is known in the art.

In addition to the standard patch-clamp electrophysiology rig 204, the Autopatcher IG system 100 includes a data acquisition system 208 and a pressure control system 212. The data acquisition system 208 relays the electrical signal of the electrophysiological data from the amplifier 210 to the computer 206 for processing and storage and may comprise any data acquisition system and/or digitizer for electrophysiology recordings (e.g., DIGIDATA 1550A or DIGIDATA 1322) (see FIG. 2b). Likewise, the pressure control system 212 functions to algorithmically control the pneumatic pressure within the pipette 221 and/or other manipulators 222. Perhaps more specifically, pneumatic pressure is sensed in the pipette 221, for example, and the pressure control system 212 operates off of a software 250-driven pump-pressure sensor feedback loop to provide automatic adjustment of the pump 238 and valves 236 of the pressure control system 212 to regulate the pressure within the pipette 221 (or other manipulator 222) and even maintain a set pressure value therein.

Figure 3A:
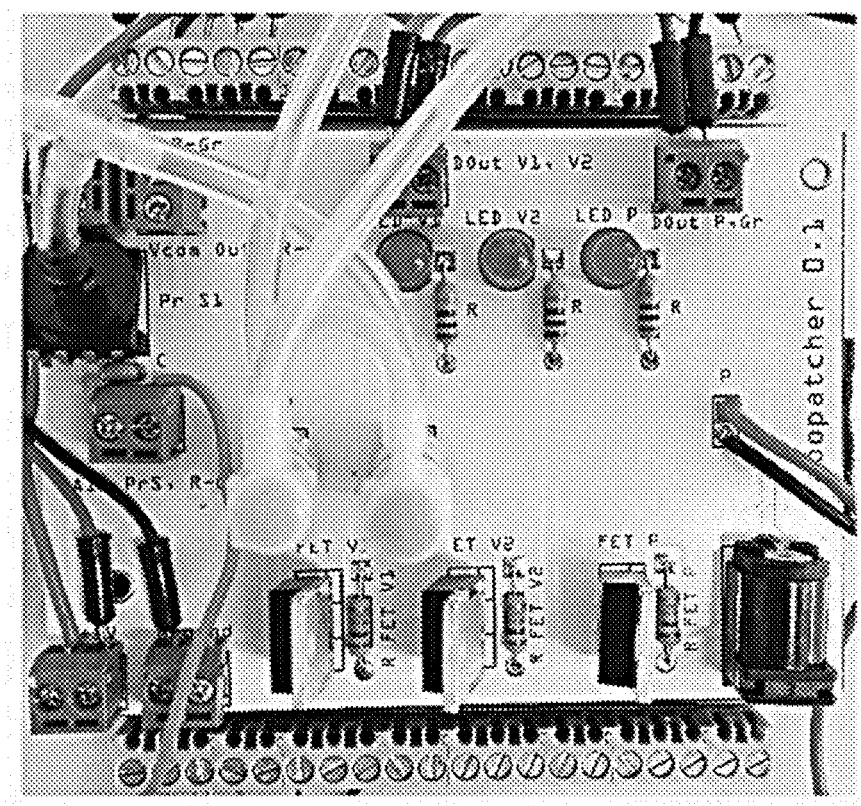
FIGS. 3*a*-3*c* show images and schematics associated with a pressure control system of the system of the present disclosure, with FIG. 3*a* showing an image of a pipette pressure control hardware, FIG. 3*b* displaying an electrical circuit map associated with the hardware of FIG. 3*a*, and FIG. 3*c* showing three different valve configurations resulting in no pressure (i), or brief pulses of positive pressure (ii) or negative pressure (iii), applied to the backend of a pipette of the system.
Figure 3B:
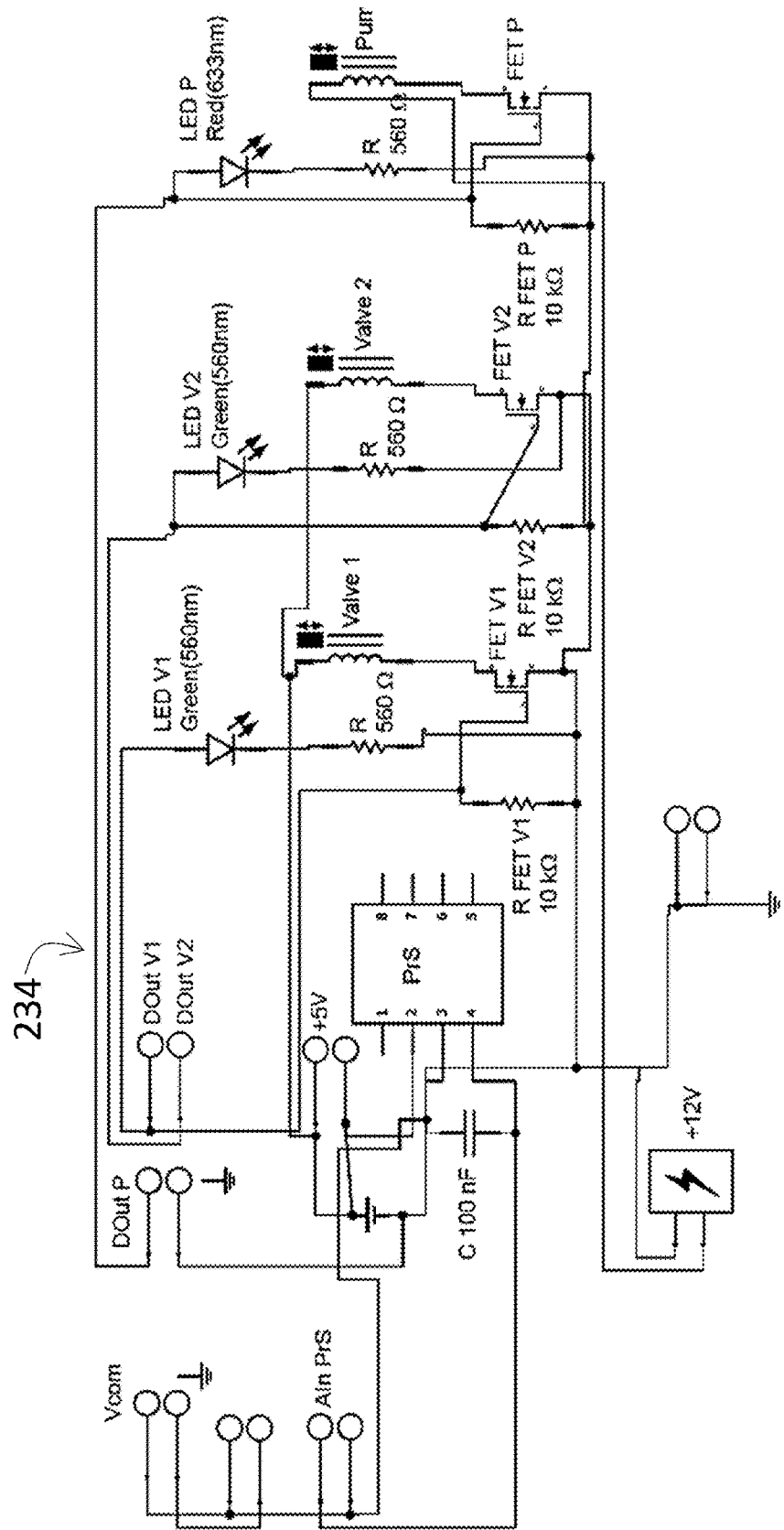
Figure 3C:
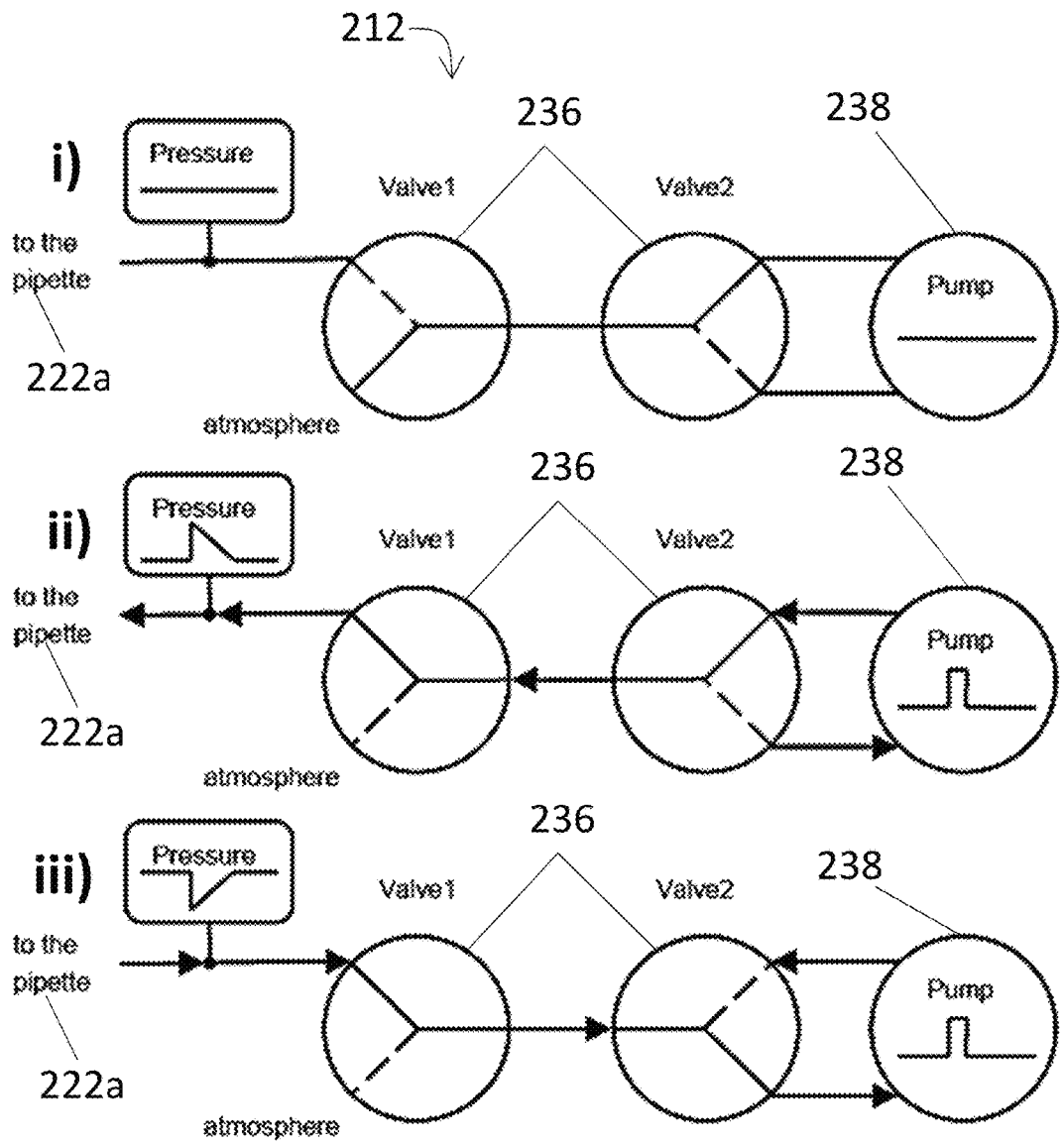

Referring to FIGS. 2b and 3a-3c, the pressure control system 212 comprises a secondary data acquisition board 234a and printed circuit board 234b that automatically control a series of valves 236, one or more air pumps 238, and an air pressure sensor 240. In at least one embodiment, the secondary data acquisition board 234 comprises Model UB1208-FS distributed by Measurement Computing Corporation (Norton, Mass.) or the like. FIG. 3a shows at least one embodiment of the hardware for a pressure control system 212, and FIG. 3c shows the electrical circuit map of the same.

By interfacing the electrophysiology rig 204 with the pressure control system 212 (e.g., via a pressure port 242 formed in the proximal end 222b of a pipette 221 and/or the holder 228 coupled therewith), the secondary data acquisition board 234 can sense (via air pressure sensor 240) and algorithmically control the pneumatic pressure within the lumen of the pipette 221 using the valves 236 and air pump(s) 238 pursuant to instructions received from the computer 206. At least three examples of potential valve 236 configurations are provided in FIG. 3c that can be used by the computer 206 to result in i) no pressure within the pipette 221; ii) brief pulses of positive pressure; or iii) negative pressure, each of which can be applied to the proximal end 22b of a micropipette 221. Alternatively, the system 100 may be configured to utilize a commercially available patch-clamp pressure control system such as, for example, the Autopatcher pressure control box manufactured by Neuromatic Devices (Atlanta, USA). In another non-limiting example, parts used to construct the pressure control system 212 may comprise a secondary data acquisition board 234 USB1208-FS, Measurement Computing, Norton, Mass.; solenoid valves 236 by The Lee Co. LHDA0531115H, an air pump 238 from Virtual Industry VMP1625MX-12-90-CH, and an air pressure sensor 240 from Freescale Semiconductor MPXV7025G.

It will be appreciated that the pressure control system 212 of the system 100 may comprise any pressure control system and/or configuration thereof if some degree of pressure control (pneumatic or otherwise) is provided within the pipette 221. Indeed, with respect to the system 100 as a whole, while specific parts and implementation details are described herein with respect to the electrophysiology rig 204 and related hardware components 202, it will be clear to one of skill in the art that many other comparable parts and implementation methodologies exist and would be equally suitable for use in the Autopatcher IG system 100.

In operation, the electrophysiology rig 204 makes whole-cell recordings, which are transferred to the computer 206 and analyzed using the software 250. For example, the tip 222a of the pipette 221 is in contact with and/or broken into an identified cell 103a and the lumen of the pipette 221 is filled with electrically conductive fluid, electrical signals from the cell 103a are transferred up the pipette 221, through the headstage 224b and into the amplifier 210 where it is amplified, and feeds into the computer 206 for processing by way of the data acquisition system 208. Similarly, suction may be applied through the pipette tip 222a to harvest contents of the cell 103a and/or substances may be injected into the cell 103 via the pipette tip 222a (e.g., fluorescence to enable visualization of the shape of the cell 103a).

Figure 4:
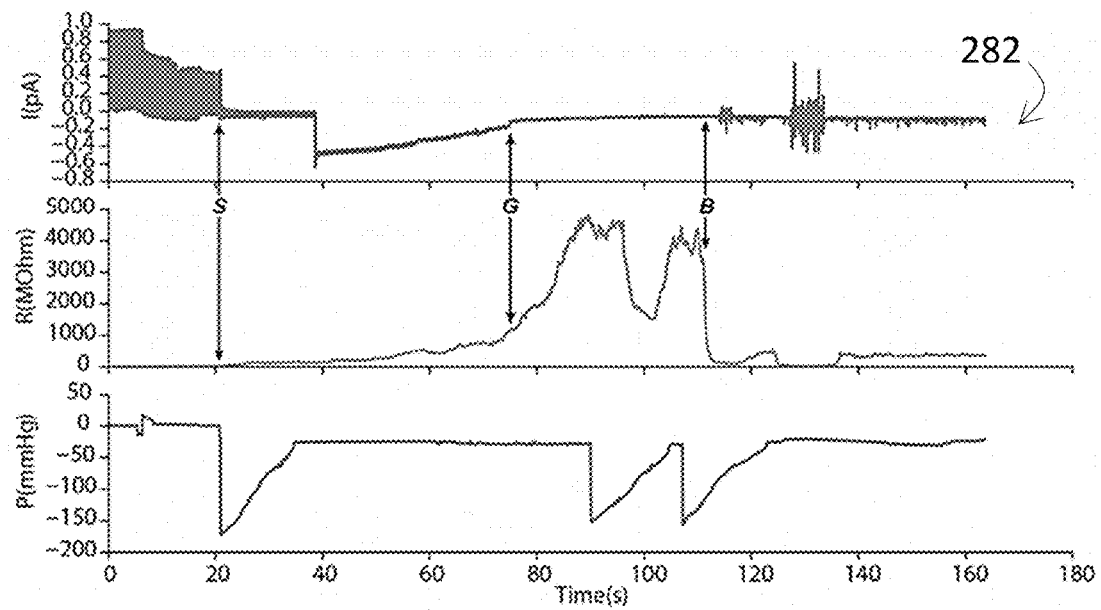
FIG. 4 shows a patch log trace resulting from the execution of a patch algorithm according to an exemplary embodiment of the present disclosure.

Based on the data collected/recorded, the software 250 (e.g., patch control module 258) automatically prepares a patch log 282 for each trial, which is a collection of images, measurements, and parameters that fully describe a whole-cell patch-clamp trial. FIG. 4 illustrates an example of patch logs 282 associated with successful patching trials, the patch logs 282 displaying a history of current (pA), resistance (MOhm), and internal pipette pressure (mmHg) parameters (with capital letters denoting the following events: S: touch cell surface, G: gigaseal, and B: break-in). The metadata included within the patch logs 282 can be mined post hoc to reveal relevant information about patch-clamp attempts such as the timing of specific steps (e.g., S, G, and B), pressures during gigasealing (G), success rates, and other characteristics of a particular trial. For example, the patch log 282 traces shown in FIG. 4 indicate an alternative patching algorithm that comprised a single large (−180 mmHg) negative pressure pulse was employed to form a gigaseal and several large negative pressure pulses were used to break-in (compare with the measured whole-cell patch properties shown in FIG. 9d from patches generated using the main patching algorithm).

The Autopatcher IG system 100 may additionally comprise one or more peripheral devices 280, such as a light source 290, a simulation isolator 292, a transistor-transistor logic ("TTL") signal-controlled device 294, and/or any other device that can interface and/or communicate with the software 250, and may be useful or desired for use in connection with the system 100. Indeed, the system 100 is configured to incorporate a scalable number of peripheral devices 280, some of which may be used for cell patching applications, while others can be employed for other purposes such as drug infusion at or near a targeted cell 103a, chemical compound uncaging using a laser beam delivered through the microscope 220 lens, and the like. In at least one embodiment, the software 250 may be programmed or updated to include additional enabling code for operating such peripheral devices 280 in conjunction with the electrophysiological rig 204 such that the automated nature of the system 100 is maintained.

As previously noted, the software 250 of the system 100 operates on the computer 206 and comprises the main graphical user interface ("GUI") 252, the command sequence module 254, memory 256, patch control module 258, and camera module 260. The software 250 provides a user-driven, sophisticated, graphical environment that enables a user to control operation of the hardware 202 for data acquisition and instrument control and/or utilize virtual instruments for data review and analysis.

Regarding a user's ability to access the functionality of the system 100, a user interacts with the system 100 through the one or more GUIs, which include, but may not necessarily be limited to, main GUI 252 and camera GUI 252a. Depending on the desired configuration and implementation of the system 100, a GUI may be local to the hardware 202, provided over a network (e.g., the Internet or a local intranet), or stored within a server or database associated with the computer 206 or a peripheral computer. In at least one embodiment, the GUIs are available through a web-based portal that provides functionality for accessing and displaying data stored within the memory 256 and/or a server. In at least one exemplary embodiment, the GUIs are part of a mobile application and/or widget designed to run on smartphones, tablet computers, wearables, and/or other mobile devices. In all cases, the GUIs are programmed to activate desired software routines and build application-specific instruments through the use of the on-screen representation of buttons, dials, toggles, fields, and sliders. In at least one embodiment, the GUIs are programmed using a dynamic programming language such as Python; however, it will be appreciated that other programming environments or general purpose programming languages (such as Java or C++) can also be used to achieve the desired GUI.

The GUIs of the system 100 are fully customizable and facilitate a user's input into and access of the functionality of the system and/or data stored therein. Initially, two separate software GUIs were generated to accommodate different setups. FIGS. 5a-5e illustrate various examples of: a) a main GUI 252, through which a user can control image acquisition, microscope stages, and micromanipulators (FIGS. 5a and 5b); and b) camera GUI(s) 252a that display camera views of a brain slice 102 with target cells 103a selected at both low and high magnification (FIGS. 5d and 5e) and the coordinates of such targeted cells 103a stored as sequences of memory positions (FIG. 5c).

It will be appreciated that while the examples of GUIs provided herein comprise specific fields, dropdown menus, data presentations, buttons, and other graphical control elements, the GUIs of the system 100 may be configured in any manner desired, customized pursuant to the particular functionalities provided by the system 1200, and/or to display various types of information and/or data analyses as appropriate or desired. Indeed, the embodiments illustrated in FIGS. 5a-5e are provided merely by way of explanatory example and are not intended to be limiting in any way.

Figure 5A:
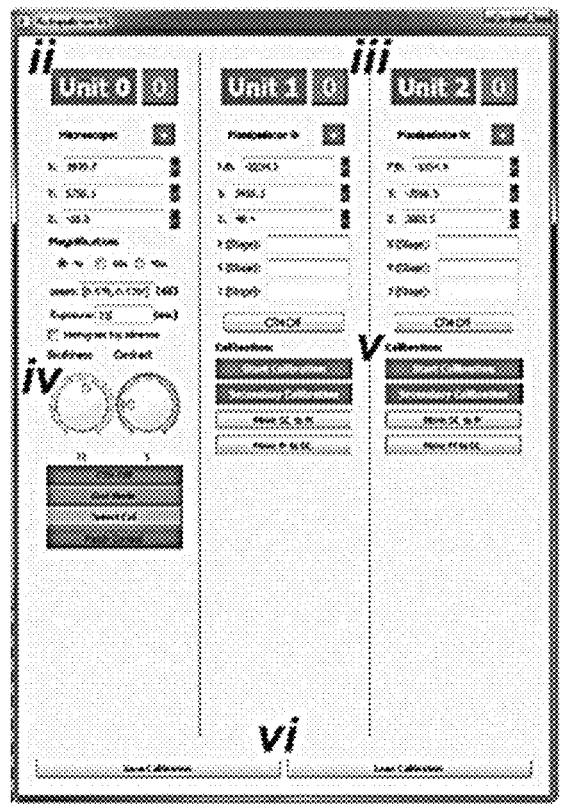
FIGS. 5*a*-5*e* show examples of graphical user interfaces according to an exemplary embodiment of the present disclosure that may be associated and/or used with the image-guided patch clamp system hereof.
Figure 5B:
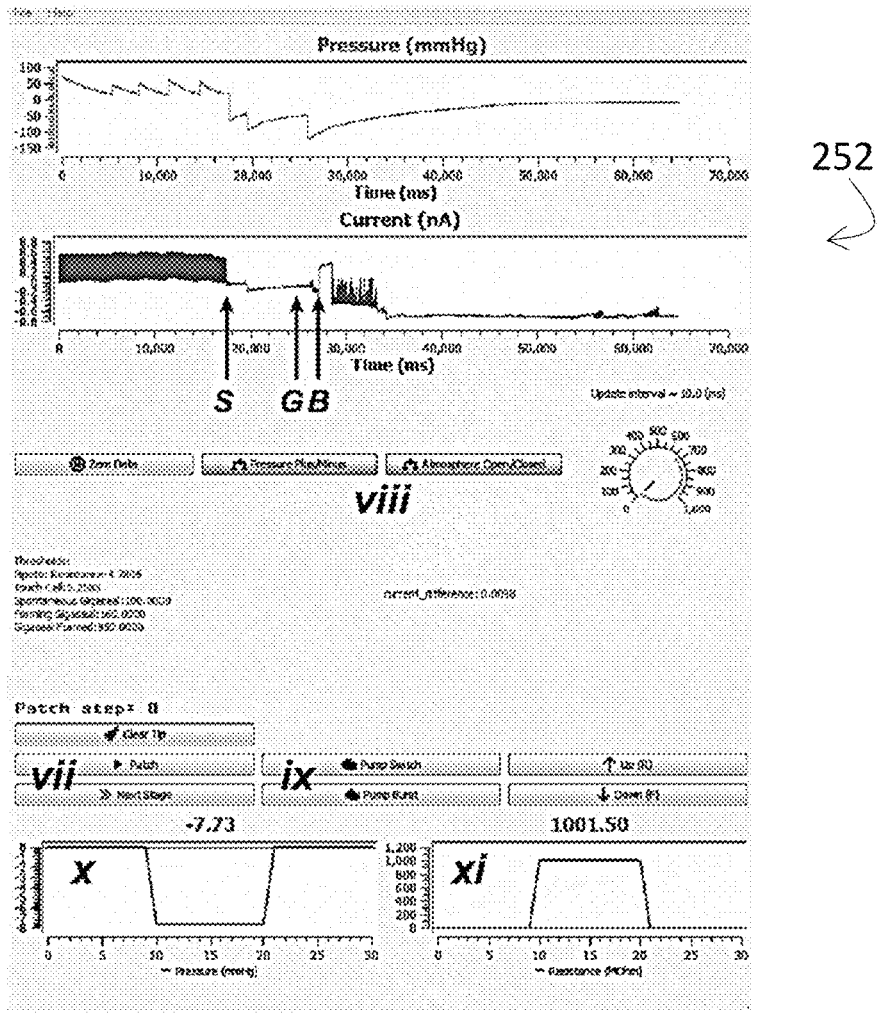
Figure 5C:
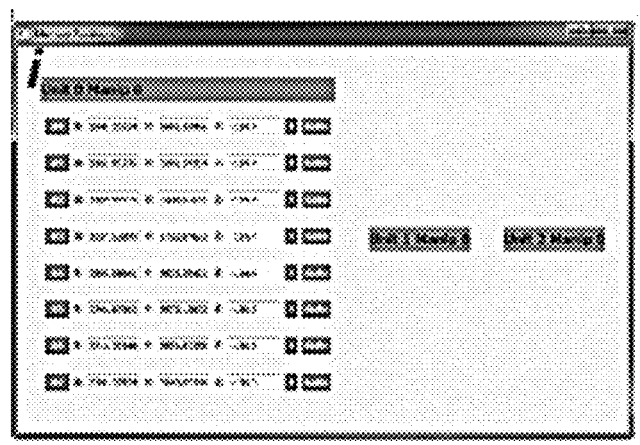
Figure 5D:
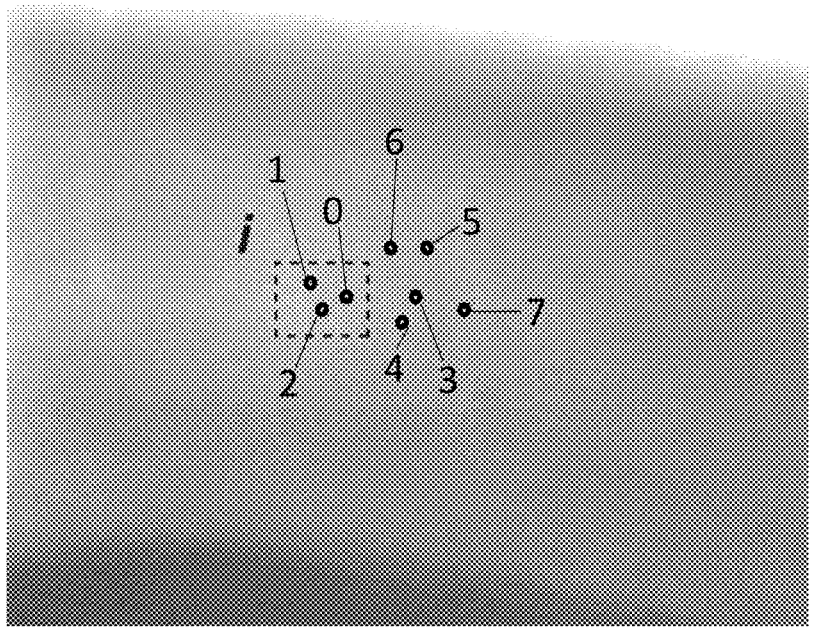
Figure 5E:
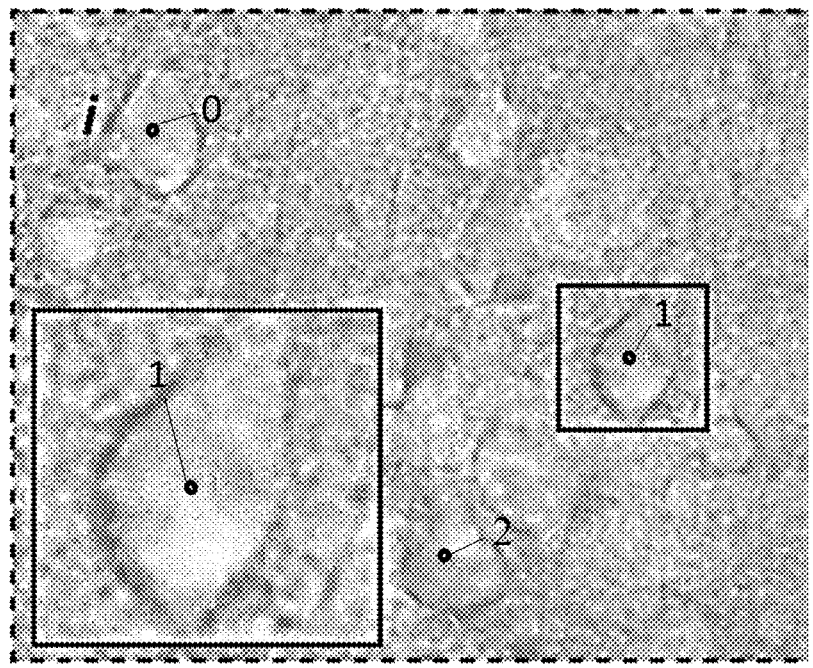

Now referring to FIGS. 5a and 5b, the main GUI 252 provides the main interface through which a user can control image acquisition, microscope stages and micromanipulators of the system 100. Examples of data and/or information displayed on at least one version of the main GUI 252 shown in FIG. 5a may include data relating to and/or representative of: a particular microscope stage 224 (ii); one or more micromanipulators 222 (iii; here, labeled "Unit 1" and "Unit 2", with additional units automatically recognized and added); camera exposure, image brightness and contrast, and/or any other captured image data (iv); automatic pipette calibration (v; here, associated with the one or more micromanipulators 222 of (iii)); and calibration save and load (vi).

Additionally or alternatively, FIG. 5b displays a patch control GUI 252 as it appears during an ongoing patching experiment. Here, (vii) represents an automatic patch algorithm, (viii) represents an independent valve configuration control, (ix) represents independent pump control, (x) represents real-time pressure data collected within a pipette 221 and (xi) represents collected resistance data. Capital letters denote important parts of the patch-clamp process, for example, S is when the pipette tip 222a touches a cell surface, G is when the gigaseal is formed with the cell 103a, and B denotes when break-in occurs. In addition to the specific GUIs 252, 252a described, additional user interfaces may include those geared towards analyzing, interpreting, and/or displaying data collected from experiments and the like, as well as any other user interface that may be desired.

In at least one embodiment of a GUI, a user can simultaneously visualize a live feed of the representative patch via a camera GUI, as well as a status bar, cell property statistics and data display and a settings display. Accordingly, while a user can visualize the patch process in real time, he or she can keep accurately apprised of what step is occurring via status bar and monitor live data on the targeted cell 103a and patching process via the constantly updating cell property statistics and data display. The particular data/statistics displayed cell the cell property statistics and data display may be customized pursuant to user preference. Additionally, a GUI may also allow a user to make adjustments to the various hardware 205 components of the system 1000 (e.g., camera 218, pipette coordinates, etc.) via a settings display. Additional examples of views and data that may be displayed via a GUI include images of a representative patched mouse neuron filled with Alexa Fluor 594 and imaged at 40× magnification, current clamp recordings of the targeted neuron, and the measured properties of whole-cell patches that are similar to that of manual patching.

Methods of performing an automated, IG patching process will now be described with reference to FIGS. 6a-8 and using the Autopatcher IG system 100 of the present disclosure. In at least one exemplary embodiment of implementing the system 100 hereof, a calibration method 600 and/or cell detection method 700 may be performed using the system 100 prior to any actual patching steps of a method 800 (or at least prior to an initial run of the method 800).

For programmable actuation of the system 100 pursuant to the various processes and methods hereof, the hardware 205 components of the system 100 may be programmable and are controlled using the software 250 (run on the computer 206 or otherwise). At least two unique algorithms may be coded in, and run by, the computer 206 and/or various other hardware components 205 of the system 100 (e.g., the data acquisition system 208) to achieve the automated functionality described herein, including a computer vision algorithm (e.g., for calibration and identifying cells), a manipulator trajectory planning and movement algorithm (e.g., for incrementally moving the manipulator 222 relative to the stage 224 and identifying and maintaining the appropriate trajectory of such movement), a patch algorithm (e.g., for performing the patching process and recordings). Additional algorithms may also be utilized by the system 100 such as an algorithm directed toward using a manipulator 222—such as a pipette 221 for example—to inject and/or release solutions, DNA, peptides, pharmaceuticals, and the like into or near a targeted cell 103a.

The computer vision algorithm is utilized in both the calibration and detection methods 600, 700 (which may be considered the set-up stages) and involves IG automated regional pipette localization and IG automated identification of neurons within a brain slice 102. The patch algorithm employs information obtained through execution of the computer vision algorithm and is utilized in executing the actual whole-cell patch method 800, which occurs in multiple stages such as: advancing the pipette tip 222a to a location at or near a targeted cell 103a (using a temporal sequence of electrode impedance changes and/or pursuant to previously recorded coordinates), forming a gigaseal using resistance and pressure feedback loops, and performing break-in. Embodiments of the calibration method 600 will be addressed first, followed by a description of the cell detection method 700 and patching method 800.

In at least one embodiment, the automated calibration method 600 is utilized to perform computer vision-aided identification of the pipette tip 222a coordinates calibration as a preliminary step of using the Autopatcher IG system 100 for whole-cell patching. Method 600 enables the software 250 to recognize and calibrate manipulator 222 position and movement with a microscope coordinate system. This calibration method 600 utilizes IG modalities, is easy to use, and can achieve a high degree of precision.

Generally, a microscope 220 is controlled by one or more motors that, during operation, utilize a microscope coordinate system to return information on its coordinates. In the Autopatcher IG system 100, a microscope 220 is used in conjunction with the computer vision algorithm to detect the position of the slice 102 and the cells 103 therein and, thus, ultimately returns data to the computer 206 relating to the microscope's 220 coordinates. Similarly, the pipette 221 (and any other manipulator 222) is controlled by one or more precision motors that utilize a separate coordinate system to track and return the coordinates of the pipette 221 during operation as perceived by the pipette coordinate system. For the system 100 to accurately direct a manipulator 222 during an automated patching process, it is necessary to determine how the manipulator(s) and microscope coordinate systems relate, so that the tip 222a of a pipette 221, for example, can accurately be moved to a precise coordinate of the microscope 220. Accordingly, through calibration method 600, the software 250 of the present disclosure derives mathematical transformation functions that align (or calibrates) the various coordinate systems associated with independent components with the coordinate system of the microscope, which serves as a "world coordinate system."

In the calibration method 600, at step 602, the computer 206 moves the manipulator 222 predefined distances along x-, y-, and z-axis through automated operation of the motorized 3-axis control 230 (and precision motor thereof), with the position of pipette tip 222a identified using the computer vision algorithm to direct each movement. The camera 218 of the system 100 captures an image of the distal end of the manipulator 222 (e.g., pipette tip 222a) through the microscope 220 each time the manipulator 222 is moved along a specific axis.

Figure 6A:
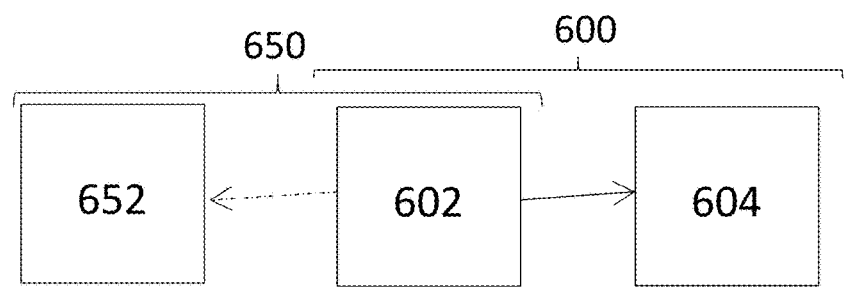
FIGS. 6*a*-6*c* show steps of a computer vision-aided calibration method according to an exemplary embodiment of the present disclosure, with FIG. 6*a* showing a flow chart representative of such method steps, FIG. 6*b* illustrating the steps of such method to identify of coordinates for a pipette tip, and FIG. 6*c* showing steps of an experiment performed to test the precision of the calibration method hereof.
Figure 6B:
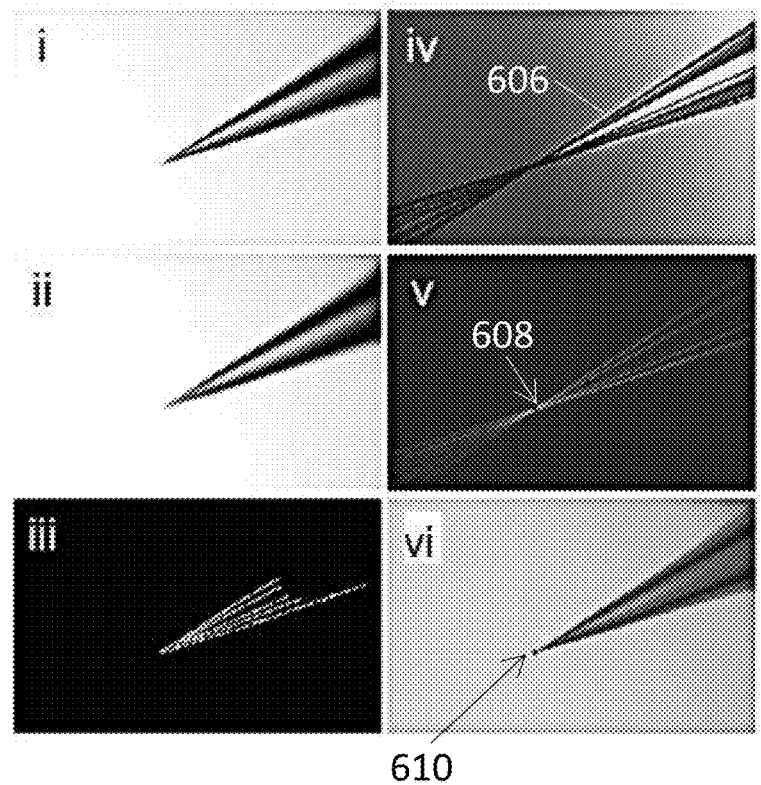

To pinpoint the coordinates of the pipette tip 222a, each image is processed at step 604 pursuant to the computer vision algorithm of the system 100. FIG. 6b depicts the steps of an exemplary embodiment of image processing at step 604 of the automated calibration method 600 pursuant to the computer vision algorithm. There, each image is first subjected to Gaussian Blur to decrease noise (panel ii) of FIG. 6b), with the result then used to extract pipette contour data using Canny Edge Detection (panel iii) of FIG. 6b). Hough Transform is subsequently applied to derive perfect lines 606 fitting the pipette contour (panel iv) of FIG. 6b), at which point the color of the image is inverted and the intensity is analyzed (panel v) of FIG. 6b). The brightest point of color 608 within the inversion image indicates where most of the pipette 221 outlines intersect, a data point that is indicative of the tip 222a coordinate 610 of the pipette 221 (panel vi) as shown in FIG. 6b). Panel i) of FIG. 6b depicts an unmodified, original pipette image for comparison purposes.

In at least one exemplary embodiment, image processing step 604 is carried out at least twice on each image, the first iteration narrowing the detection range to a small cropped image near the tentative coordinate of the pipette tip 222a and the second iteration determining the final pipette tip 222a coordinate 610. Dual processing is beneficial in terms of accuracy as it accounts for potential changes in the angle of the glass pipette wall at different distances from the tip 222a that may occur due to variations that may be present in the shape of the pipette 221 in the image that result from the pulling parameters. Furthermore, for calibration along the z-axis, focus detection may be applied prior to the computer vision processing to derive a third pipette tip 222a coordinate. Focus detection may be performed pursuant to a focus detection algorithm and includes, for example, image detection together with change-of-focus performed by the z-motor of the microscope 220.

Figure 6C:
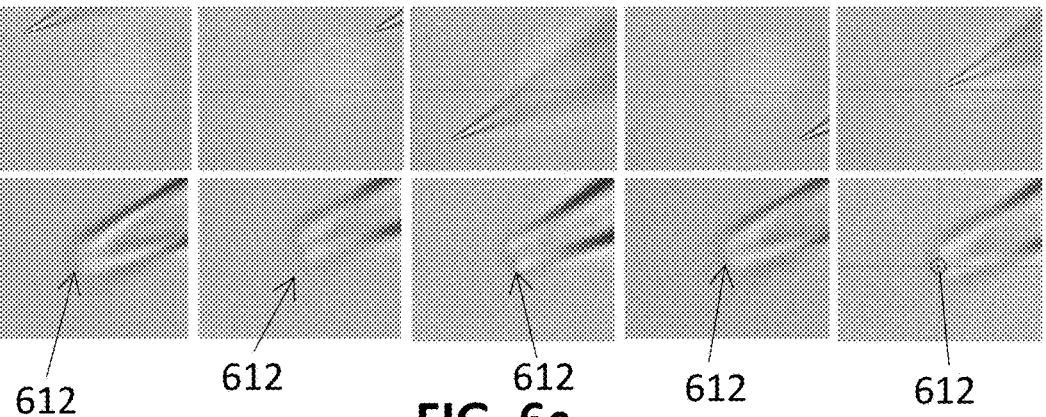

The automated calibration method 600 takes, on average, about 1 minute and 8 seconds±6 seconds (mean±standard error of mean, n=10 trials) to complete and the average error was about 1.6 µm (SE=0.215 µm, n=10 trials) when the pipette traveling distance was within a 200 µm radius after calibration. FIG. 6c shows images of a test calibration performed to assess the precision of the automatic pipette calibration of the present system 100, as compared to manual methodologies. In this trial, a pre-defined calibration grid was used and the pipette tip 222a was targeted to the centroids of four quadrants and the screen center. The upper panel (panel 1) shows the relative location of the pipette tip 222a in the screen at 4× magnification and the lower panel (panel 2) shows the precision of the pipette placement at 40× magnification. Each dot 612 in an image of panel 2 represents one pixel in size and is the target location. In addition, all automatic patching experiments described in the present disclosure used the same primary calibration coefficients that were saved and reloaded each day. There was no observable deterioration in performance, given that the hardware 202 set-up of the system 100 was stable (the angle and magnitude of manipulator movement relative to the microscope view did not change). As illustrated in FIG. 6c, in addition to being quick and easy to perform, the automatic IG calibration process of the Autopatcher IG system 100 is highly accurate.

After performing the automated calibration method 600, the trajectory of the manipulator 222/pipette 221 can be controlled via a graphic user interface associated with the system 100 (for example, "Memory Positions" GUI 252a described below, which accesses the target coordinates stored in the memory 256 of the system 100), a keyboard, a mouse, or any other input device coupled with the system 100. In certain exemplary embodiments, the automatic patching examples described below with respect to method 800 utilize memorized/stored target cell coordinates to direct both microscope 220 and pipette 221 to the target cell 103a. After calibration using method 600, the pipette 221 does not need to be located within the microscope view for targeting and positioning.

The initial calibration method 600 need only be performed once upon initial setup of the electrophysiological rig 204 or at any time the hardware configuration is changed (e.g., if the angles of the manipulator 222 set-up are changed). The initial calibration method 600 is not required each time the system 100 is used to perform a trial using method 800 (described below) since the transformation coefficient does not change unless the hardware 202 configuration is altered. Instead, for repeated patch trials using method 800 and the same hardware 202 configuration of system 100, the only calibration effort that may be required is optional secondary calibration process 650 designed to correct for any coordinate offset resulting from differences in pipette 221 length that may arise due to replacement of an existing pipette 221 with a new one. This secondary calibration process 650 re-aligns the two coordinate systems (i.e. microscope and manipulator coordinate systems) by performing step 602 (detecting the pipette tip 222a through the microscope 220 using the computer vision algorithm after each movement) and, at step 652, re-applying transformation coefficients that were obtained in step 604 from the initial calibration process 600.

Now referring to FIGS. 7a-7c, 7g, and 7h, an automated, IG detection method 700 is also provided. Generally, the cell detection method 700 comprises the steps of automatically detecting a cell 103 having a fluorescent signal at step 702, determining the coordinates of the cell 103 at step 704, and storing the determined coordinates at step 706 for use in subsequent patch clamp experiments (method 800) or otherwise. The automation of cell detection is achieved, at least in part, by using computer vision and executing the computer vision algorithm to process images acquired with epifluorescence optics, detect fluorescent neurons 103 therein, and ultimately identify their x-, y-, z-coordinates at different slice depths.

Figure 7A:
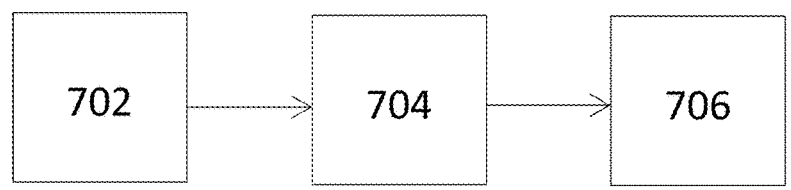
FIGS. 7*a*-7*f* show steps of, and associated data resulting from, a computer automated, image-guided detection method according to an exemplary embodiment of the present disclosure, with FIG. 7*a* showing a flow chart representative of such method steps, FIG. 7*b* showing images acquired with epifluorescence optics and the steps of the detection method applied thereto to identify fluorescent neurons and their x-, y-, z-coordinates, FIG. 7*c* showing a representative patched fluorescent neuron from an acute brain slice, post fixed, immunolabeled with anti-GFP antibody, FIG. 7*d* displaying a graphical representation of current clamp recordings of a patched cell responding to hyperpolarizing and depolarizing current injection, FIG. 7*e* showing a graphical representation of how the neuron of FIG. 7*d* reacts to light (480 nm) activation with bursts of action potentials (arrows showing the light-on epochs that are 2 ms each and 150 ms apart), and FIG. 7*f* showing patched cell properties measured from each successful trial (no differences were observed as compared to non-fluorescent cells in FIGS. 10*a*-10*d*.
Figure 7B:
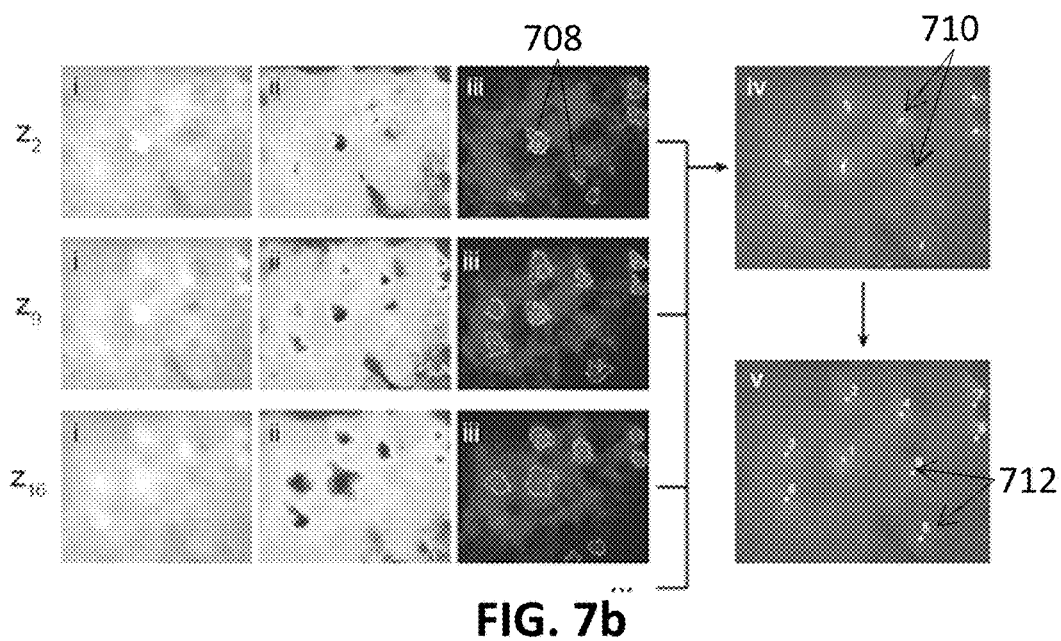

At step 702 of the method 700, the computer vision algorithm controls the microscope stage 224 to acquire a series of images at different z-sections (e.g., a default setting may include 20 images, 2 µm z-step size). FIG. 7b shows three representative z-sections from a complete experiment (20 z-sections) using brain slices prepared from a mouse expressing Channelrhodopsin-2-EYFP in layer 5 pyramidal cells. Likewise, FIG. 7g shows three representative z-sections from a complete experiment using brain slices prepared from mice injected with HSV-ArchT-EGFP. Each acquired image is transformed into a series of black and white images using different thresholds (0.5× to 5× of mean pixel intensity). These thresholds are customizable and may be established by a user, automatically programmed into the system 100, or established via some variation of the foregoing. The use of multiple thresholds (as opposed to a single threshold) ensures that the algorithm can accommodate a wide range of fluorescent intensity. Images i) of FIGS. 7b and 7g show the original image after histogram equalization and images ii) show a pseudo-colored image after thresholding.

At step 704, the images are further processed using initial Canny Edge Detection or any other suitable image processing modality, and cell contours identified within a defined size and circularity range are each deemed a tentative cell. Images iii) of FIGS. 7b and 7g show superimposed cell-like contours 708 detected after a series of varying thresholds (similar to perfect lines 606 of method 600). Centroids 710 from these tentative cell contours 708 from different thresholds are then identified and clustered into groups based on their distance from each other (see images iv) showing the centroids 710 of detected contours 708 that were accumulated from the z-sections). A defined threshold of a minimal number of detected centroids 710 in a cluster may be used to detect and exclude false positives. The final coordinates 712 of each detected cell 103 are calculated as the mean of all centroid 710 coordinates along the x- and y-axes, and the median along the z-axis (see images v).

The resulting cell coordinates 712 are stored by the system 100 at step 706; saved in a file or otherwise (e.g., stored in memory 256 or a database in communication with the computer 206). These coordinates 712 may be displayed to a user in the GUI 252a (labeled "Memory Positions" in FIG. 5c) and also used to direct a patch pipette 221 and/or other manipulators 222a and/or peripheral devices 280 of the system 100. For example, in at least one embodiment, a puff pipette 280 may be used with the electrophysiology rig 204 for local drug application, for single-cell laser-scanning photostimulation, or chemical compound uncaging.

The computer vision algorithm according to the present disclosure was validated with respect to detecting fluorescent cells in both cortical slices made from a Thy1-Channelrhodopsin 2-EYFP (Thy1-ChR2-EYFP) transgenic mouse (line 18) and from a wild type mouse injected with HSV-ArchT-GFP virus. The average time of detection was 84.2±0.9 seconds for Arch-GFP (n=10) and 89.3±1.3 seconds for Thy1-ChR2-EYFP (n=10). The average number of false positives, i.e. registered coordinates 712 that do not represent a cell 103, was low for both preparations, 0.6±0.3 cells and 0.2±0.1 cells for HSV-ArchT-GFP and Thy1-ChR2-EYFP respectively. The detection threshold range and computing power may affect total detection time; however, they were sufficient for the standard desktop computer used in the experiments. The low variation identified in the experiments demonstrates that the automated system 100 and detection method 700 using the same are robust and stable.

The system 100 was also used to demonstrate the feasibility of complete automatic patching from cell detection (method 700) to form whole-cell configuration (method 800, described below) using the Autopatcher IG system 100. The goal of this experiment was to verify the accuracy of the system's 100 ability to automatically target GFP-positive neurons in a transgenic mouse expressing light-sensitive channelrhodopsin-2 in the layer 5 pyramidal cells through performance of method 700. A targeted subpopulation of these layer 5 pyramidal cells are intrinsically bursting cells, which means they burst in response to internal step current injection.

Figure 7C:
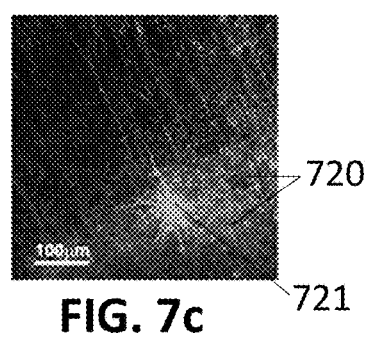
Figure 7D:
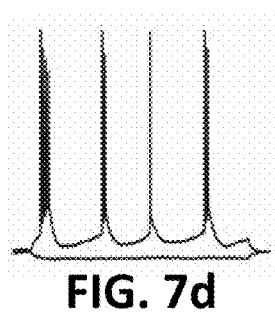
Figure 7E:
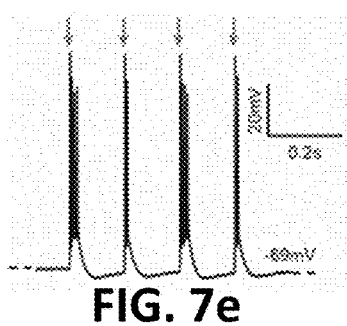
Figure 7F:
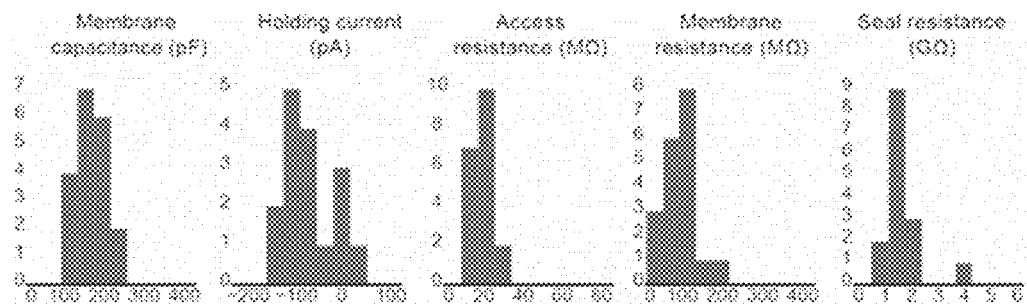
Figure 7G:
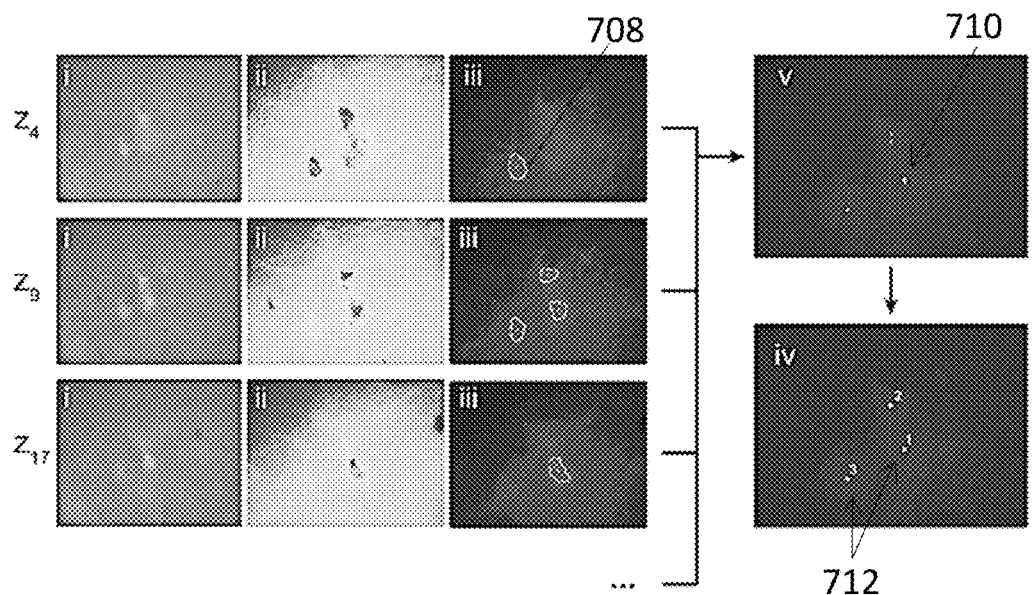
FIGS. 7*g*-7*i* show steps of, and associated data resulting from, a computer automated, image-guided detection method according to an exemplary embodiment of the present disclosure in connection with ArchT-EGFP-positive cells, with FIG. 7*g* showing images representative of the steps of the detection method applied thereto to detect fluorescent cells and their x-, y-, z-coordinates and indicative that this method also works for HSV-ArchT-EGFP injected mice, FIG. 7*h* showing a representative confocal microscopy image of a ArchT-EGFP-positive cell filled with Alexa Fluor 568, post fixed, and immunolabeled with anti-GFP antibody, and FIG. 7*i* displaying a graphical representation of current clamp recording trace of a bursting cell hyperpolarized in response to light (550 nm) activation (represented by the green bar)

20 whole-cell patches were formed from fluorescent-positive layer 5 neurons in Thy1-ChR2-EYFP cortical slices (FIG. 7c showing an image acquired using confocal microscopy of a representative patched fluorescent neuron 720 (green in original, color version) filled with Alexa Fluor 568 dye 721 (red in original, color version) in layer 5 mouse neocortex and FIG. 7d showing current clamp recordings of a patched cell responding to hyperpolarizing and depolarizing current injection). The clamp recordings of FIG. 7d are characteristic of a layer 5 intrinsically bursting (IB) pyramidal neuron, thus supporting accurate cell detection by the method 700. The average time for pipette positioning was 98.5±2.8 seconds, forming gigaseal was 136.5±20.1 seconds, and break-in was 9.8±2.8 seconds, all of which were not significantly different from automatic and semi-automatic patching trials in WT mice (p>0.4 for all). Patched cells were subjected to light activation to confirm ChR2-EYFP expression, the results of such study displayed in FIG. 7e. The patch qualities were consistent with WT patches (FIG. 7f). With reference to FIG. 7f, patched cell properties measured from each successful trial are provided. No differences were observed compared to non-fluorescent cells in FIGS. 10a-10d.

Figure 7H:
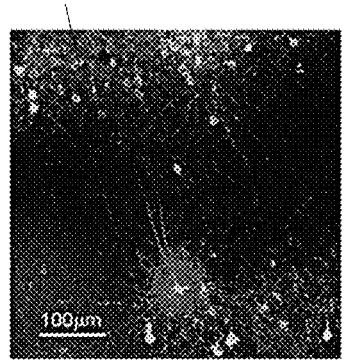
Figure 7I:
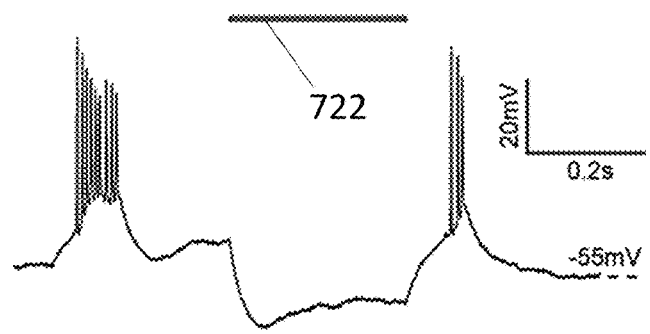

Similarly, FIGS. 7h and 7i show images depicting the results associated with the automated computer vision processing of images pursuant to the present disclosure to detect fluorescent cells in the HSV-ArchT-EGFP injected mice. FIG. 7h displays an image acquired using confocal microscopy that represents a ArchT-EGFP-positive cell 720 filled with Alexa Fluor 568, post fixed, immunolabeled with anti-GFP antibody (cell 720 displaying green in original color version; a ArchT-EGFP being a fusion of a light-sensitive hyperpolarizing ion pump and a green fluorescent protein). FIG. 7i shows a representative current clamp recording trace of a bursting cell hyperpolarized in response to light (550 nm) activation (bar 722). These results again support that performance of the automated method 700 by system 100 can successfully detect and patch a green cell expressing ArchT-EGFP.

Figure 8A:
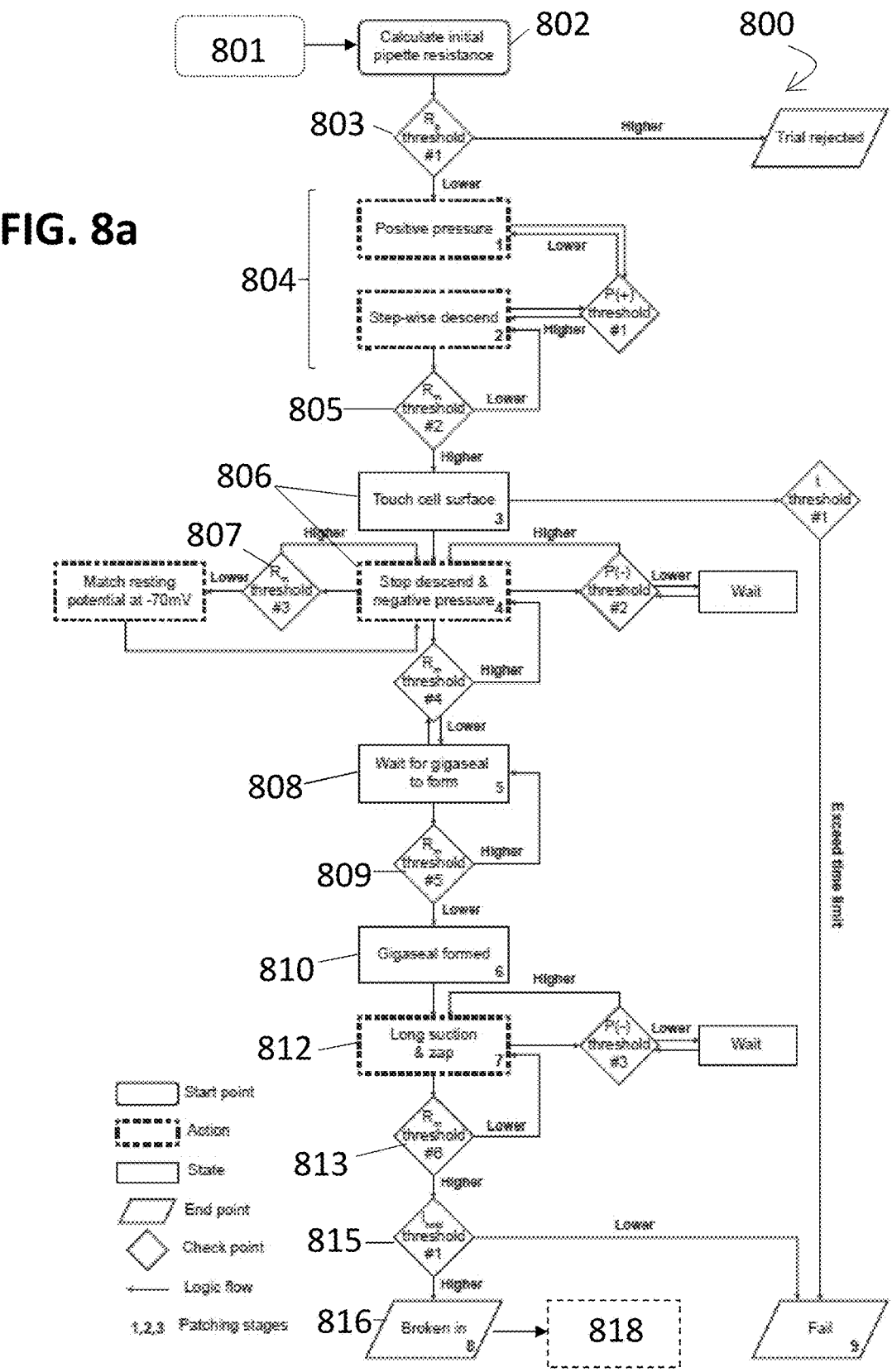
FIG. 8*a* shows a flow chart representative of an patch function algorithm logic utilizing a patch algorithm according to an exemplary embodiment of the present disclosure.

Methods of performing an automated, IG patching process will now be described with reference to FIGS. 8a and 8b and using the Autopatcher IG system 100 of the present disclosure. In at least one exemplary embodiment of such an automated method 800, a patch control algorithm of the patch control module 258 automatizes the patching process by defining distinct stages and determining transitions between these stages by a series of pipette resistance and pressure threshold configurations, the values of which can be modified and updated by submitting an input file to the computer 206 at any time during the process and pursuant to user preference or otherwise. For reference, in FIG. 8a, defined stages are shown in solid boundary rectangles and transitions therebetween are determined by resistance and pressure thresholds shown in diamond squares (i.e. each a "check point"). Each threshold or check point can be changed and updated at any time by a user using data input (via a GUI 252 or otherwise into the computer 206). Each action is shown in a dashed rectangle and is executed with the corresponding check point(s), which instruct the software 250 to either loop back or proceed to the next state. Furthermore, it will be appreciated that method 800 may be performed on its own, following, or in series with initial calibration method 600 and/or secondary calibration method 650 as may be appropriate or desired (preliminary step 801). FIG. 8b provides a table of exemplary default threshold values useful in method 800, with all listed thresholds relating to the threshold or check point values shown in FIG. 8a (however, it will be noted that any of these values may be changed by a user and saved to the system 100 in a configuration file).

At preliminary step 801 of method 800 (not shown), a target cell 103a is selected (using detection method 700 or otherwise) and initial pipette resistance ($R_p$) 803 is calculated as a reference point to establish a membrane resistance ($R_m$) threshold 805. Upon initiation of a patching trial (by a user clicking a "Patch" button in a main GUI 252, for example) at step 802, the manipulator 222 moves to coordinates 712 (established using methods 600 and/or 650 or otherwise), which may optionally be offset by a user-defined "final approach" distance. In at least one embodiment, this user-defined "final approach" distance comprises 10 µm, but it may be changed and/or established at any value based on user preference. The user can then choose to approach the cell 103a either along the shortest trajectory, or vertically along the z-axis (all specific results described in the present disclosure were acquired using the vertical approach option).

Upon reaching the "final approach" distance, the patch control module 258 commands the manipulator 222 to descend towards a selected cell 103a in small, predefined increments (e.g., about 1 µm) at step 804. During the manipulator's 222 descent, any resistance change at or near the tip 222a of the pipette 221 is closely monitored (using, for example, using the pressure control system 212). This may be achieved by emitting a series of membrane test current injections or through other methods now known or hereinafter developed. For example, in at least one embodiment, a small positive pressure (about 35 mmHg to about 60 mmHg, as default) may be maintained within the lumen of the glass pipette 221 through operation of the pressure control system 212 via a pump-pressure sensor feedback loop. When an increase in the pipette resistance over the defined membrane resistance threshold 805 is detected (e.g., a 15% increase over initial pipette resistance, $R_p$, as default), the method 800 automatically advances to step 806. However, if the threshold 805 is not met, the step-wise descent of the manipulator 222 is continued and, in at least one embodiment, pressure is maintained.

At step 806, the tip 222a of the manipulator 222 automatically ceases its descent and, pursuant to the resistance reading, is positioned at or near the targeted cell 103a. Furthermore, in at least one embodiment, the valve 236 configuration of the pressure control system 212 is automatically switched to apply negative pressure to the pipette 221 in order to facilitate formation of a gigaseal.

At step 808, the patch control module 258 maintains negative pressure (e.g., about −60 mmHg to about −100 mmHg, as default) within the pipette 221 through the pressure control loop of the pressure control system 212. When the next resistance threshold 807 is reached (e.g., 90 MΩ), the holding voltage potential is decreased to match the cell resting membrane potential (e.g., to around −70 mV). The gigasealing algorithm then ceases the application of negative pressure through the pipette 221 and waits for formation of a gigaseal with the targeted cell 103a at step 810 (which may be defined by satisfying resistance threshold 809 and/or $R_p$ being >1 GΩ).

After the gigaseal is formed, the method 800 does not automatically advance, but instead prompts the user at step 812 to provide feedback as to the desired next step. In at least one embodiment, the prompt of step 812 comprises the option to apply long suction and/or zap (i.e. a brief voltage pulse applied to the cell to establish a whole cell state) or, alternatively, perform a procedure defined as the default procedure to achieve break-in. For example, in at least one embodiment, the default break-in procedure is defined as applying pulses of negative pressure to the targeted cell 103a until the resistance threshold 813 is satisfied (e.g., cell membrane resistance falls to less than about 300 MΩ and the holding current is within the range of −200 pA to +100 pA), which is indicative of advancement to step 816—that break-in was successful and whole-cell configuration is established. Additionally, successful patches may be validated using threshold 815 by measuring resting potential (<−55 mV) and step current injection induced action potentials (see FIG. 10c, for example). If the user opts for the default break-in process (either by affirmatively selecting the same or not responding to the prompt within a pre-set period of time), system 100 will automatically perform the process set as default to achieve step 816. Upon receiving the user's selection or when the pre-set period of time has passed, the method advances to step 816 where break-in is achieved pursuant to the appropriate method and whole-cell configuration is established.

If the success criteria or any intermediate thresholds 805, 807, 809, 813 are not met, the method 800 remains in the current stage/step and continues to execute the respective action until exceeding a specified time limit (e.g., 4 min as default; denoted in FIG. 8a as "t threshold" or "Trial rejected"). At step 818, all pressure and resistance parameters are recorded and saved as patch logs 282 for use post hoc analysis for experiment quality control and/or configuration optimization. Furthermore, as previously noted, the system 100 is scalable and allows for automated patching and recording of two or more cells simultaneously (see FIGS. 10e-10h).

In one embodiment, all trials are initiated automatically. However, apart from the automatic gigasealing algorithm, a user can interfere to control the pump 238, the valves 236, and the manipulators 222. For example, any human interventions can be introduced into the system 100 via a modified algorithm and automated. Any trials with user intervention are classified as semi-automatic.

Figure 9B:
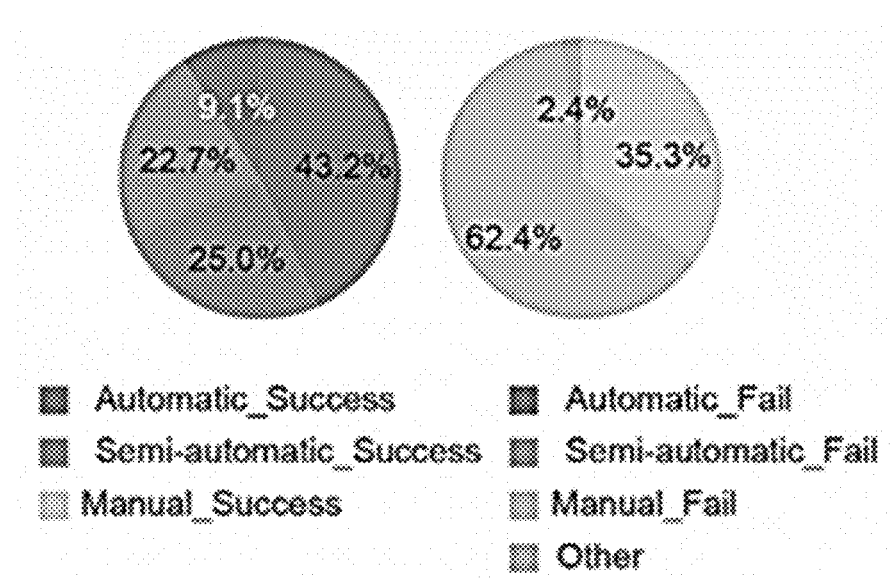
Figure 9C:
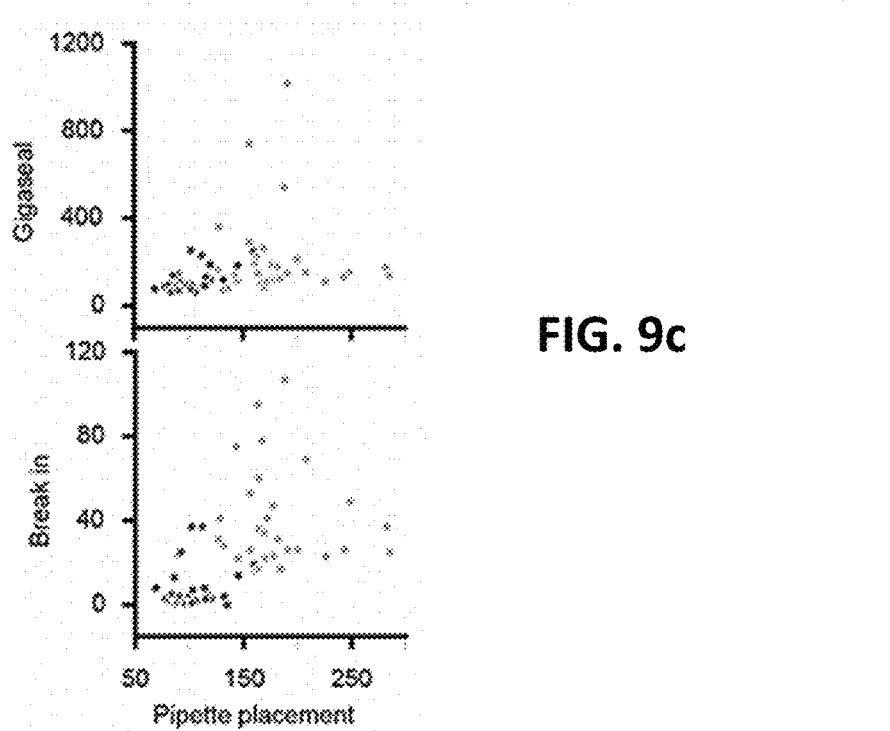
Figure 9D:
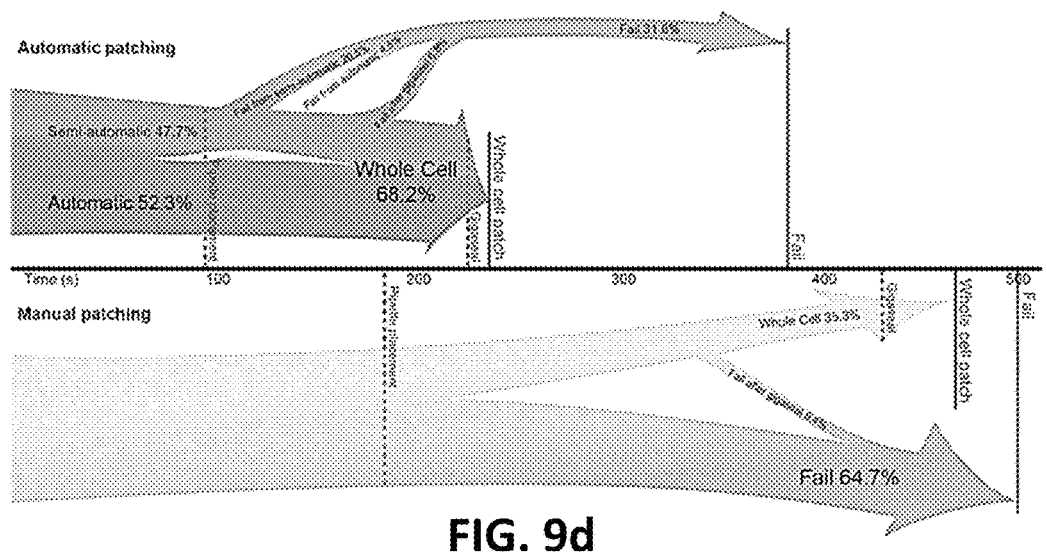

To show enablement, patch clamp experiments were conducted both automatically and manually to evaluate the efficiency and effectiveness of the Autopatcher IG system 100 and the methods of using the same. Thirty successful whole-cell configurations were achieved in 44 automatic/semiautomatic patching trials with a total success rate of 68.2%, while the success rate by manual patching was only 35.3% (30 out of 85 trials). Among all 44 trials using the Autopatcher IG system 100, 23 trials (52.3%) were fully automatic and 19 trials resulted in successful patches, which accounted for 82.6% in fully automatic subcategory or 43.2% in total. The other 21 trials out of the total 44 (47.7%) were semi-automatic, 11 of which resulted in successful patch. This accounts for 52.4% in the semi-automatic subcategory and 25.0% as compared to the total (FIGS. 9b and 9d). Both fully automatic and semi-automatic patching yielded higher success rate compared to manual patching.

Figure 10A:
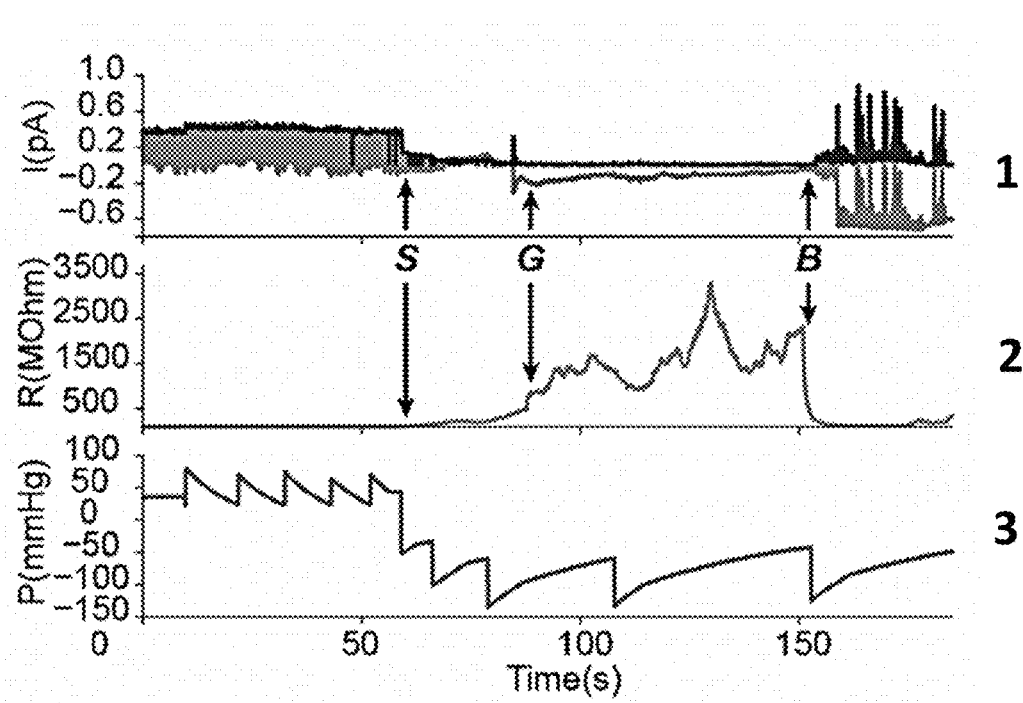
FIG. 10a shows a patch log of a successful patching trial with a history of current (pA), resistance (MOhm), and internal pipette pressure (mmHg) parameters (upper panel representing raw voltage input from the data acquisition board (light) and the membrane test current (dark), the middle panel representing membrane resistance, and the lower panel representing internal pipette pressure)
Figure 10B:
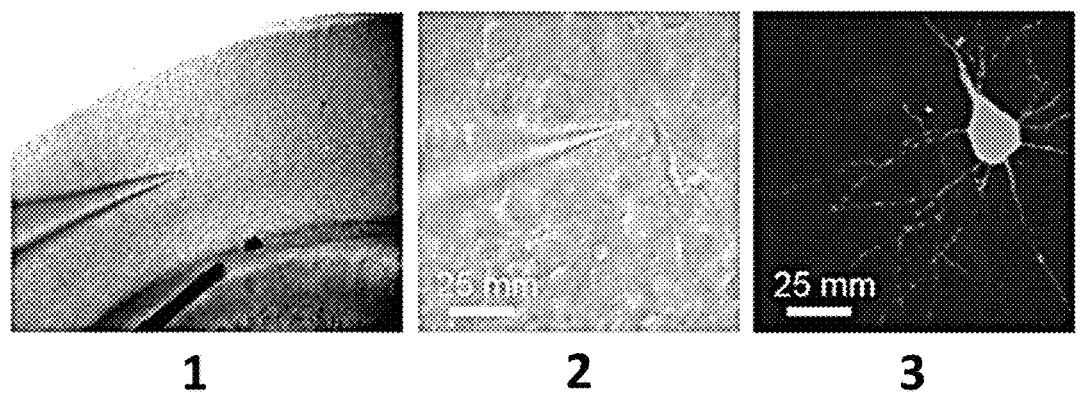
FIG. 10b show representative images of an automatically patched cell according to an exemplary embodiment of the present disclosure at 4× magnification (left) and 40× magnification DIC optics (middle) in a mouse visual cortex brain slice (right panel shows the same neuron filled with Lucifer Yellow, post-fixed and visualized with 40× magnification epifluorescence optics)
Figure 10C:
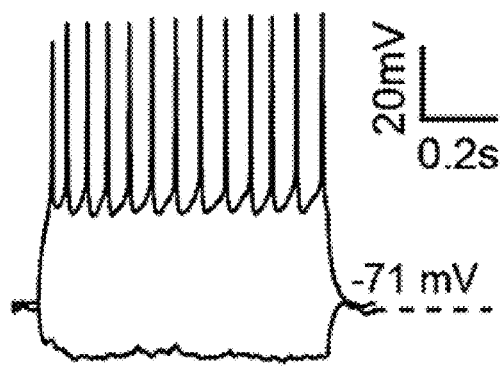
FIG. 10c shows a graphical representation of electrophysiological responses of an automatically patch-clamped neuron to hyperpolarizing and depolarizing current injections.
Figure 10D:
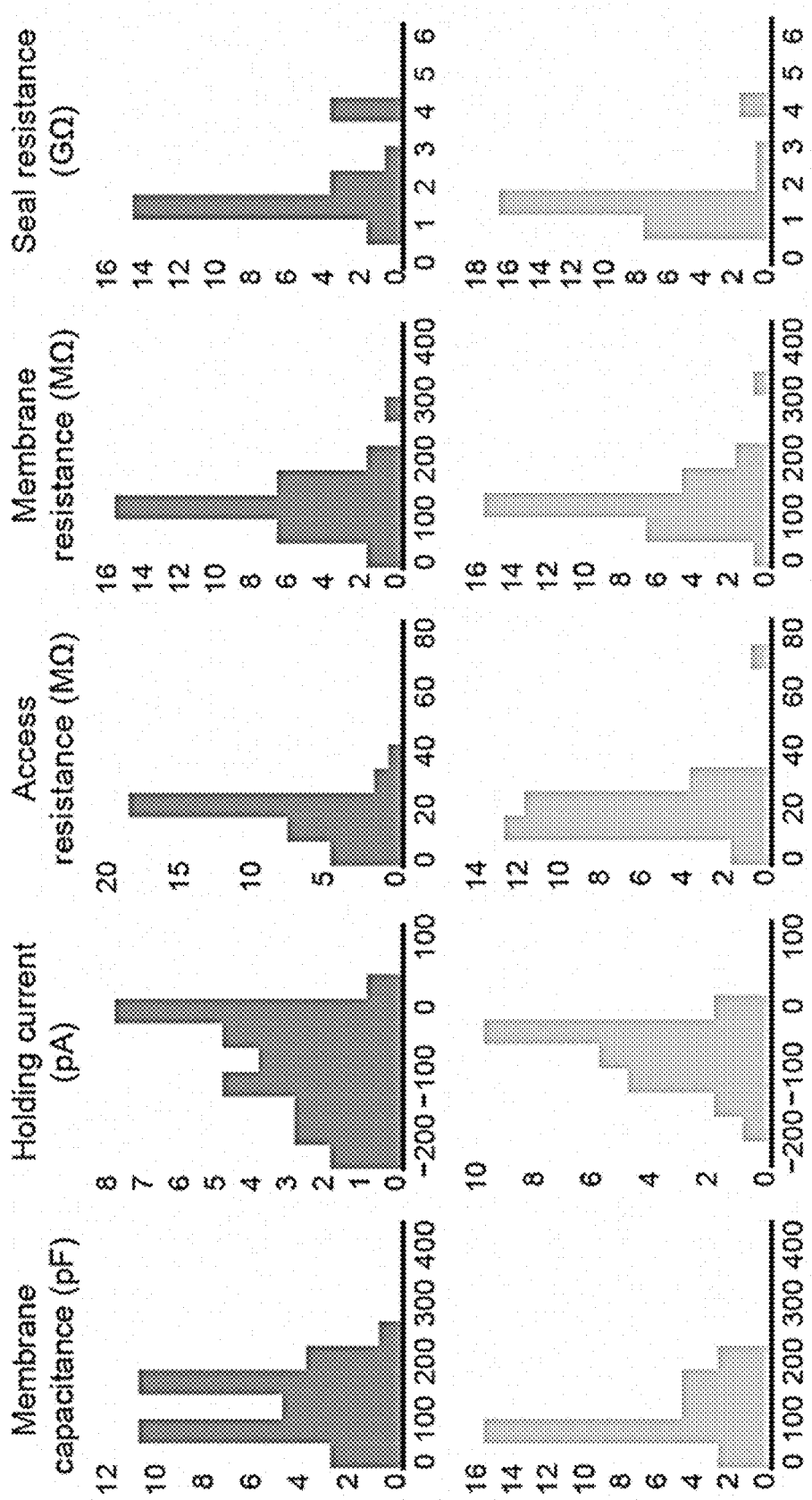
FIG. 10d shows graphical representations of data supporting that automatic patching generates high quality patches that are at least comparable in quality to conventional manual patching (top row representing automatic patching and bottom row representing manual patching)

FIGS. 10a-10d further support that the automatic, IG patch clamp system 100 of the present disclosure yields high quality whole-cell recordings comparable with the manual patch. Indeed, there was no significant difference in the quality of patches obtained using the two methods, based on the seal resistance, the membrane capacitance and resistance, the access resistance, and the holding current (FIG. 10d). FIG. 10a shows an example patch log 282 of a successful patching trial with a history of current (pA), resistance (M$\Omega$), and internal pipette pressure (mmHg) parameters. The upper panel (panel 1) represents raw voltage input from the data acquisition board 208 (grey) and the membrane test current (black). The middle panel (panel 2) represents membrane resistance and the lower panel (panel 3) represents internal pipette pressure. Capital letters denote: S: touch cell surface, G: gigaseal, and B: break-in.

Likewise, FIG. 10b provides representative images that show an automatically patched cell at 4× magnification (left, image 1) and 40× magnification DIC optics (middle, image 2) in a mouse visual cortex brain slice 102. Right panel (image 3) shows the same neuron 103 filled with Lucifer Yellow, post-fixed and visualized with 40× magnification using the microscope 220. FIG. 10c depicts graphical data representative of an automatically patch-clamped neuron's 103 electrophysiological responses to hyperpolarizing and depolarizing current injections delivered by the manipulator 222 of the system 100. Finally, the graphical data shown in FIG. 10d supports that automatic patching generates high quality patches that are comparable in quality to conventional manual patching. Specifically, the top row of graphs (row 1) represents data collected from an automatic patching trial performed by the system 100 and the lower low of graphs (row 2) represents manual patching.

Similarly, FIGS. 10e-10h illustrate data relating to the successful use of method 800 for automated patching and recording of two or more cells simultaneously. FIG. 10e shows a representative image of two simultaneously patched cells in a slice 102, and FIG. 10f shows a confocal image of the two cells shown in FIG. 10e filled with Alexa 568 hydrazide (light portion shows red in original color image) and fixed after patching. FIG. 10g shows a graph of the electrophysiological responses of these two patched cells to hyperpolarizing and depolarizing current injections, with the upper panel representative of the data for the cell on the left (marked L) and the lower panel representative of the data for the cell on the right (marked R). Finally, FIG. 10h shows data for simultaneous recordings of excitatory postsynaptic potentials (EPSPs) from these two neurons 103a evoked by white matter (WM) stimulation.

In addition to the success rate, the average times for positioning a pipette tip next to a target cell, forming a gigaseal, and breaking-in were significantly shorter using the systems and methods of the present disclosure, as compared to manual patching (FIGS. 10a and 10d). Moving a pipette tip 222a to a saved target cell 103a location, using both preliminary and secondary calibration methods 600, 650, took on average 103.2 seconds (SE=2.7) for both fully automatic and semi-automatic trials (no difference at this stage). This was dramatically faster as compared to manual pipette tip 222a placement, which took 183.0±4.4 seconds (p-value<10e-24). Furthermore, using automatic manipulator control and memory positions 256 allowed for pipette tip 222a placement outside of the microscope 220 visual field, which is impossible using manual patching.

Use of the automatic patch-clamp algorithm hereof in conjunction with the system 100 and method 800 also resulted in faster gigaseal formation, taking (a) 119.5±18.3 seconds for the fully automatic approach; (b) 122.6±10.1 seconds for semi-automatic patching (difference between the two was not significant, p=0.88); and (c) 233.6±30.3 seconds for manual patching (p-value=0.001). At least in part, precise, fast pressure control in response to resistance changes significantly decreased the break-in time from 49.1±8.1 seconds for manual trials, to 15.3±4.3 seconds for semi-automatic trials (p-value=0.024) and 5.2±1.0 seconds for fully automatic trials (p-value<0.0002). There was no significant difference between the duration of failed trials for either automatic or manual algorithms. However, because the duration of a successful trial was two times shorter, and the success rate was two times higher, the overall time spent to achieve comparable productivity was much shorter for the automatic algorithm. Autopatcher IG aided patching was also more consistent, because the time spent during each automatic trial was less variable compared to manual patching (FIG. 9c).

Figure 11:
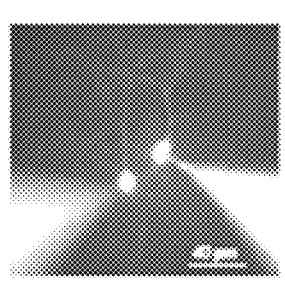
FIG. 11 displays a high-level diagram showing the components of an exemplary data-processing system 1000 for analyzing data and performing the methods hereof according to an exemplary embodiment of the present disclosure.
Figure 11:
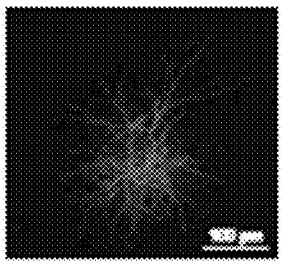
Figure 11:
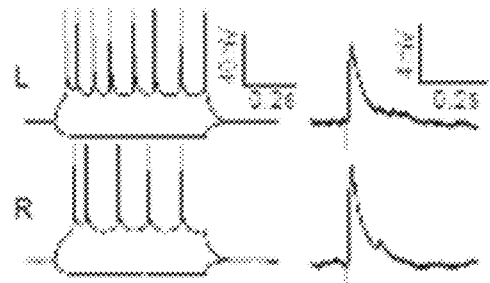
Figure 11:
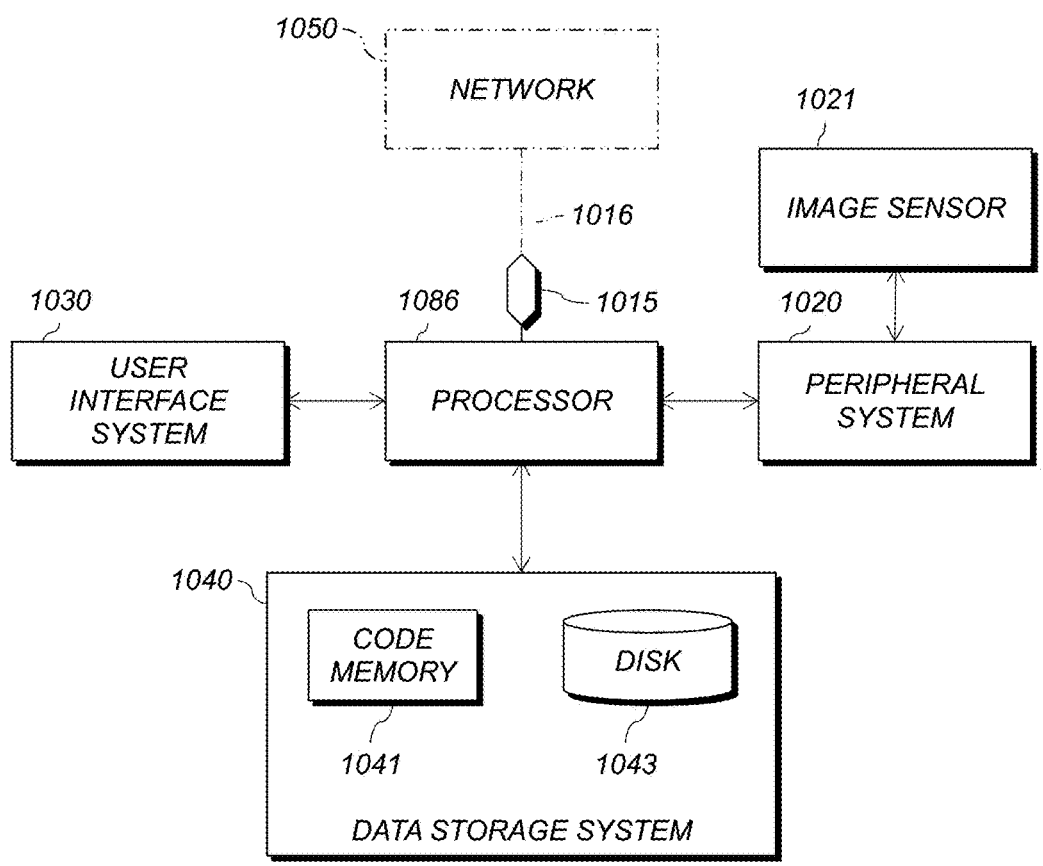

Referring to FIG. 11, a high-level diagram showing the components of an exemplary data-processing system 1000 for analyzing data and performing other analyses described herein, and related components are provided. The system 1000 includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), which may comprise the Internet or a leased line, as described below. The imaging and 3D point data described herein may be obtained using imaging sensors 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 can implement processes of various aspects described herein (for example, and without limitation, methods 600, 650, 700, and/or 800). Processor 1086 can be or include computer 206 of the Autopatcher IG system 100, which may comprise one or more device(s) for automatically accessing and/or operating on data, e.g., a central processing unit (CPU), microcontroller (MCU), desktop computer, laptop computer, mainframe computer, personal digital assistant, server computer, digital camera, cellular phone, smartphone, tablet, or any other device for displaying data, processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices and/or processors. These devices or processors can be located in physical proximity or not. For example, subsystems such as peripheral system 1020, user interface system 1030, and data storage system 1040 are shown separately from the data processing system 1086, but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors (including, without limitation, electrophysiology rig 204 and the various components thereof, pressure control system 212, peripheral devices 280 and/or other components associated with any of the aforementioned). The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086 (using, for example in at least one embodiment, software 250). The user interface system 1030 also can include a display device, a processor-accessible memory, or any device or combination of devices to which data is output by the processor 1086. The user interface system 1030 and the data storage system 1040 can, in at least one embodiment, share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 and network 1050. Network link 1016 can be connected to network 1050 via a switch, gateway, hub, router, or other networking device.

Processor 1086 is configured to send messages and receive data, including program code, through network 1050, network link 1016 and communication interface 1015. For example, a server can store requested code for an application program (e.g., a JAVA applet), which may comprise a software module, application, code, or the like of software 250, on a tangible nonvolatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 (i.e. memory 256) can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041 and, as a result, causes performance of the method steps by the system 100 as described herein. In this way, processor 1086 carries out a computer 206 implemented process of methods 600, 650, 700, and 800. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

With respect to the specific examples and experiments described herein, both male and female animals were used in acute brain slice preparation, as were C57BL/6 (wild type) mice (except for testing fluorescent cell detection and the patching algorithm). Visual cortical slices from young (P21-P50) mice were prepared pursuant to known methodologies. Mice were anesthetized using isoflurane, and decapitated following confirmation of deep anesthesia using tests of corneal reflex and toe pinch. The brain was removed and sliced using a vibrating-blade microtome (Leica Microsystems, Buffalo Grove, Ill.) in an ice-cold oxygenated high-sucrose dissection buffer containing (in mM): 75 sucrose, 10 glucose, 87 NaCl, 2.5 KCl, 1.25 NaH$_2$PO$_4$, 25 NaHCO$_3$, 0.5 CaCl$_2$, 7 MgCl$_2$, 1.3 ascorbic acid. Coronal 350 μm slices containing primary visual cortex were incubated at 32° C. for 15 minutes in a holding chamber with oxygenated artificial cerebrospinal fluid (ACSF) containing (in mM): 124 NaCl, 3.5 KCl, 1 CaCl$_2$, 0.8 MgCl$_2$, 1.23 NaH$_2$PO$_4$, 26 NaHCO$_3$, and 10 glucose, and subsequently incubated at 30° C. for the remainder of the day.

Acute brain slices were prepared from adult (P50-P180) mice using the protective recovery method known in the art. Briefly, animals were heavily anesthetized with isofluorane and perfused trans-cardially with an NMDG solution containing (in mM): 93 N-methyl-D-glucamine (NMDG), 2.5 KCl, 1.2 NaH$_2$PO$_4$, 30 NaHCO$_3$, 20 HEPES, 25 Glucose, 5 Na-ascorbate, 3 Na-pyruvate, 10 MgSO$_4$.7H2O, 0.5 CaCl$_2$.2H2O (pH titrated to 7.3-7.4, osmolarity: 300-310). Mice were quickly decapitated, the brain was extracted, embedded in 2% agarose and cut into 300 μm coronal slices using a VF200 compresstome (Precisionary Instruments) in the cutting solution. The slices were incubated at 34° C. in the cutting solution for 10-121 minutes and then transferred to a recovery solution containing (in mM) 92 NaCl, 2.5 KCl, 1.2 NaH$_2$PO$_4$, 30 NaHCO$_3$, 20 HEPES, 25 Glucose, 5 Na-ascorbate, 2 Thiourea, 3 Na-pyruvate, 2 MgSO$_4$.7H2O, 2 CaCl$_2$.2H2O (pH: 7.3-7.4, osmolarity: 300-310) for at least 60 minutes prior to beginning recording. Recordings were performed at room temperature (25° C.) in an open bath chamber (RC-29, Warner Instruments) with standard recording solution containing (in mM): 124 NaCl, 2.5 KCl, 1.2 NaH$_2$PO$_4$, 24 NaHCO$_3$, 5 HEPES, 12.5 Glucose, 2 MgSO$_4$.7H2O, 2 CaCl$_2$.2H2O. The liquid junction potential was not corrected.

In all preparations, patch-clamp electrodes were pulled from filamented borosilicate glass tubes (BF 150-86-10, Sutter Instruments) using a P-97 micropipette puller (Sutter Instruments) to a resistance of 3.5-7.9 MΩ. Internal solution contained (in mM): 20 KCl, 100 K-gluconate, 10 HEPES, 4 MgATP, 0.3 Na$_2$PO$_4$GTP, 7 phosphocreatine, and 0.2% biocytin with pH adjusted to 7.4 and osmolarity adjusted to 300 mOsm. In some experiments, 4% w/v Alexa Fluor 594 (A-10438, Life Technologies) or Lucifer Yellow (L-453, Life Technologies) were added to the intracellular solution to visualize patch-clamped cells under fluorescent optics. Cell characteristics were obtained 5 min after a successful break-in using Clampex. The algorithm was considered to yield a successful whole-cell recording if R$_a$ is less than 80 mΩ and I$_{hold}$ at −70 mV is larger than −200 pA.

All data is reported as mean±standard error of mean (s.e.m.). Two-tailed student T test was used to compare between groups, with p<0.05 considered significant.

For cell labeling with fluorescent dye, a glass pipette (with filament) was back filled with 5 mM Alexa Fluor 568 in 5 nM KCl by contacting the back of the glass pipette (opposite side of the tip) with the dye solution such that a small volume of the dye solution filled the tip of the pipette by capillary force. The pipette was then back-filled with internal solution. Patch clamp experiments were then performed as described and the cell was held for at least 30 min after whole-cell configuration was formed to allow the dye to diffuse into the projections.

With respect to details regarding immunohistochemistry and imaging, acute brain slices were fixed in 4% paraformaldehyde solution for 30 min at room temperature, washed with PBS three times over 1 hour, and subjected to antibody labeling or directly mounted for imaging. Chicken anti-GFP (ab13970, abcam) 1:1000 in PBS with 5% bovine serum albumin and 0.1% Triton X 100 overnight at 4° C. to label channel rhodopsin-EYFP was used. Slices were washed in PBS three times over 1 hour and incubated with goat anti-chicken Alexa 488 (A-11039, Thermal Fisher) overnight at 4° C. in the same buffer as primary antibody labeling. Slices were then washed and mounted for imaging with confocal scanning microscopy (Zeiss LSM710).

For the examples herein comprising viral injection surgery, Arch T-EYFP was cloned into the HSV amplicon vector p1006, under the control of the mCMV promoter and packaged using the standard amplicon packaging protocol. The titer was 3×10$^8$ infectious units (i.u.)/ml. C57BL/6 wild type mice P16 to P25 were used to inject HSV-Arch-GFP in the primary visual cortex. Animals were initially anesthetized with 5% isoflurane and 1.5% during the surgery. The surgical site was shaved and disinfected with 75% ethanol. The skin above the visual cortex was surgically removed and connective tissue was removed with 3% hydrogen peroxide. Four craniotomies (two per hemisphere) at the primary visual cortex (coordinates determined by a mouse brain atlas) were carefully drilled by robotic rodent stereotactic surgery system (Neurostar). 500 nl of virus were injected to each site at 0.6 mm depth spanning 10 min. The surgical site was sealed locally with Kwik-Cast Sealant (WPI) and then the skull was sealed with dental cement (Ortho-jet, Lang Dental). Animals recovered for 2-3 days before acute cortical slices preparation to allow for optimum protein expression. The procedure previously described above was then performed to prepare acute brain slices.

While various embodiments of the Autopatcher IG system 100 and methods 600, 650, 700, and 800 of using the same have been described in considerable detail herein, the embodiments are merely offered as non-limiting examples of the disclosure. It will therefore be understood that various changes and modifications may be made, and equivalents may be substituted for elements thereof, without departing from the scope of the present disclosure. The present disclosure is not intended to be exhaustive or limiting with respect to the content thereof. Along these lines, it will also be understood that while specific experimental methods and materials are described, such description is provided to support an enabling disclosure and not intended to be limiting in any way. Indeed, while specific examples are described, one of skill in the art will appreciate variations on the disclosed scientific methodologies that can still make use of the inventive devices, systems, and concepts of the present disclosure, as well as other methods/materials that may be substituted for any particular examples set forth herein.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and remain within the scope of the present disclosure.

The invention claimed is:

1. An automated vision system configured for use with an apparatus for cell patch clamping, the system comprising:
    a camera system configured to provide images of in vitro tissue positioned on a stage of an apparatus for cell patch clamping; and a computer comprising a processor, the computer in communication with the camera system and configured to:
receive a plurality of images of the tissue positioned on the stage from the camera system;
detect a plurality of cells in each image;
extract coordinates of each of the plurality of cells from each image; and
provide the coordinates to a stage controller of the apparatus for cell patch clamping to:
automatically move a manipulator coupled with the stage controller to a position directly above each of the plurality of cells, and
initiate and control an automated patch-clamp process, performed by the apparatus for cell patch clamping, for each of the plurality of cells.

2. The automated vision system of claim 1, further comprising a pressure control system in operative communication with the computer and a pressure sensor coupled with the manipulator of the apparatus for cell patch clamping, the pressure control system comprising a pump in fluid communication with one or more valves.

3. The automated vision system of claim 1, wherein the camera system is coupled with a microscope of the apparatus for cell patch clamping.

4. The automated vision system of claim 1, wherein the tissue comprises a brain slice and the plurality of cells comprise living neurons.

5. The automated vision system of claim 1, wherein detecting a plurality of cells in each image further comprises:
transforming the plurality of images into corresponding black and white images that apply a plurality of predetermined multiples of mean pixel intensities;
extracting contours of various shapes in the black and white images and establishing forms of the various shapes by identifying edges of the various shapes; and
identifying targeted cells based on predetermined size and circularity associated with a centroid of each of the various shapes.

6. The automated vision system of claim 5, wherein providing the coordinates to a stage controller further comprises:
clustering centroids into groups based on distance and abundance measurements; and
calculating a mean of all centroids in a respective cluster according to a standardized coordinate system.

7. The automated vision system of claim 6, wherein clustering centroids into groups further comprises superimposing and clustering centroids along x- and y-dimensions.

8. The automated vision system of claim 3, further comprising a computer usable medium having a computer readable program code embodied therein for causing the computer to operate the camera system and the apparatus for cell patch clamping, the computer readable program code executable by the processor and comprising:
a computer readable program code means for operating the camera system;
a computer readable program code means for operating the apparatus for cell patch clamping;
a computer readable program code means for acquiring data from the apparatus for cell patch clamping; and
a computer readable program code means for analyzing images received from the camera system and data received from the apparatus for cell patch clamping and displaying analysis to a user.

9. The automated vision system of claim 8, wherein the computer is further configured to calibrate a position of the manipulator relative to a coordinate system of the microscope and the computer readable program code further comprises a computer readable program code means for calibrating the position of the manipulator from the plurality of images received from the camera system.

10. The automated vision system of claim 9, wherein calibration of the manipulator comprises:
using the camera system to acquire an image of the tip of the manipulator each time the tip is iteratively moved a predefined distance along a x-, y-, or z-dimension; and
processing each image of the tip to identify a data point indicative of a coordinate of the tip of the manipulator, the step of processing comprising the steps of:
transforming the image into a corresponding black and white image by applying a plurality of predetermined multiples of mean pixel intensities;
extracting contour lines of the tip in the black and white image, and
identifying a point where the contour lines intersect;
wherein the point where the contour lines intersect is the coordinate of the tip of the manipulator.

11. A method for performing whole-cell patch clamping in vitro comprising the steps of:
using a camera system to capture images of in vitro tissue positioned on a stage of an apparatus for cell patch clamping;
accessing the images with a computer, the computer comprising a processor and in communication with the apparatus for cell patch clamping;
detecting a plurality of cells in each image using the computer;
extracting coordinates of each of the plurality of cells from each image, each of the coordinates associated with a position of a cell on a microscope stage of the apparatus for cell patch clamping; and
moving a tip of a manipulator of the apparatus for cell patch clamping to a position directly above a targeted cell within the plurality of cells, the position of the tip based on one or more of the coordinates; and
initiating the apparatus for cell patch clamping to perform an automated patch clamp process for the targeted cell, at least one step of the patch clamp process controlled by the computer.

12. The method of claim 11, further comprising the steps of:
receiving, on the computer, data from the apparatus for cell patch clamping; and
analyzing, using the computer, the received data into one or more patch logs;
wherein each of the images captured by the camera system are captured at a different z-section of the in vitro tissue.

13. The method of claim 11, wherein the computer is in operative communication with a pressure control system and a pressure sensor coupled with the manipulator and the automated patch clamp process further comprises the steps of:
iteratively lowering the tip of the manipulator;
operating the pressure control system to apply positive pressure through the tip of the manipulator;
measuring the resistance at the tip after each iteration of the lowering step;

determining if a cell has been encountered by the tip by taking into account the coordinates and the resistance measurements after each iteration of the lowering step;
iteratively continuing the steps of lowering and determining until the resistance measurement satisfies a first pre-set threshold value; and
when the resistance measurement satisfies the first pre-set threshold value, operating the pressure control system to apply negative pressure to the targeted cell through the tip of the manipulator;
wherein the lowering, measuring, and determining steps are automated and controlled by the computer.

14. The method of claim 13, further comprising the step of initiating the formation of a gigaseal between the tip of the manipulator and the targeted cell by continuing the step of operating the pressure control system to apply negative pressure to the targeted cell until the resistance measurement satisfies a second pre-set threshold value and, when the resistance measurement satisfies the second pre-set threshold value, operating the pressure control system to match a holding voltage potential of the manipulator with a resting membrane potential of the targeted cell, and ceasing the application of negative pressure to the targeted cell.

15. The method of claim 14, further comprising the steps of:
prompting a user to select a process for establishing a whole-cell patch clamp configuration from one or more options comprising a long suction approach, a zap approach, and a combination of a long suction and zap approach; and
performing the process for establishing a whole-cell patch clamp configuration pursuant to the user-selected option; or
if the user does not select an option within a pre-set period of time, performing the process for establishing a whole-cell patch clamp configuration pursuant to a pre-set default option.

16. The method of claim 11, wherein the detection step further comprises:
transforming each image into a corresponding black and white image by applying a plurality of predetermined multiples of mean pixel intensities;
extracting contours of various shapes in each black and white image and establishing forms of the various shapes by identifying edges of the various shapes; and
identifying targeted cells based on predetermined size and circularity associated with a centroid of each of the various shapes.

17. The method of claim 16, wherein the step of moving a tip of a manipulator further comprises the steps of:
clustering centroids into groups based on distance and abundance measurements by superimposing and clustering centroids along x- and y-dimensions; and
calculating a mean of all centroids in a respective cluster according to a standardized coordinate system.

18. The method of claim 11, further comprising the steps of:
using the camera system to acquire an image of the tip of the manipulator each time the tip is iteratively moved a predefined distance along a x-, y-, or z-dimension; and
processing each image to identify a data point indicative of a coordinate of the tip of the manipulator, the step of processing comprising the steps of:
transforming the image into a corresponding black and white image by applying a plurality of predetermined multiples of mean pixel intensities;
extracting contour lines of the tip in the black and white image, and
identifying a point where the contour lines intersect;
wherein the point where the contour lines intersect is the coordinate of the tip of the manipulator.

19. The method of claim 18, wherein the processing step is performed at least two times for each image.

20. An automated vision system configured for use with an apparatus for cell patch clamping, the system comprising:
a camera system configured to provide images and operate in conjunction with an apparatus for cell patch clamping; and
a computer configured for operable communication with the camera system, an apparatus for cell patch clamping, and a pressure control system in fluid communication with a pressure sensor coupled with a manipulator of the apparatus for cell patch clamping, the computer comprising a processor and a computer usable medium having computer readable program code embodied therein for causing the computer to operate the camera system, the pressure control system, and the apparatus for cell patch clamping, the computer readable program code executable by the processor and comprising:
a computer readable program code means for operating the camera system to capture images;
a computer readable program code means for operating the apparatus for cell patch clamping to perform whole-cell patch clamp processes and recordings on a plurality of cells within in vitro tissue positioned on a stage of the apparatus for cell patch clamping;
a computer readable program code means for operating the pressure control system to apply positive or negative pressure through, or maintain the pressure of, the manipulator of the apparatus for cell patch clamping;
a computer readable program code means for receiving data from the apparatus for cell patch clamping;
a computer readable program code means for receiving images captured by the camera system; and
a computer readable program code means for analyzing images and data received from the camera system and apparatus for cell patch clamping.

\* \* \* \* \*